(12) United States Patent
Chen et al.

(10) Patent No.: US 11,213,529 B2
(45) Date of Patent: Jan. 4, 2022

(54) SALT OF SUBSTITUTED UREA DERIVATIVE AND USE THEREOF IN MEDICINE

(71) Applicant: SUNSHINE LAKE PHARMA CO. LTD., Guandong (CN)

(72) Inventors: Liang Chen, Dongguan (CN); Chengxi Li, Dongguan (CN); Bing Liu, Dongguan (CN); Yingjun Zhang, Dongguan (CN); Changchung Cheng, Cambridge, MA (US)

(73) Assignee: SUNSHINE LAKE PHARMA CO., LTD., Guandong (CN)

( * ) Notice: Subject to any disclaimer, the term of this patent is extended or adjusted under 35 U.S.C. 154(b) by 38 days.

(21) Appl. No.: 16/628,233

(22) PCT Filed: Jul. 11, 2018

(86) PCT No.: PCT/CN2018/095241
§ 371 (c)(1),
(2) Date: Jan. 2, 2020

(87) PCT Pub. No.: WO2019/011264
PCT Pub. Date: Jan. 17, 2019

(65) Prior Publication Data
US 2020/0121690 A1 Apr. 23, 2020

(30) Foreign Application Priority Data
Jul. 13, 2017 (CN) .......... 201710569633.8

(51) Int. Cl.
*A61K 31/5377* (2006.01)
*A61K 45/06* (2006.01)
*C07D 413/12* (2006.01)

(52) U.S. Cl.
CPC .......... *A61K 31/5377* (2013.01); *A61K 45/06* (2013.01); *C07D 413/12* (2013.01)

(58) Field of Classification Search
None
See application file for complete search history.

(56) References Cited

U.S. PATENT DOCUMENTS

| 10,065,934 | B2 | 9/2018 | Cheng et al. |
| 2008/0027076 | A1 | 1/2008 | Jones et al. |
| 2008/0108608 | A1 | 5/2008 | Jones et al. |
| 2008/0153838 | A1 | 6/2008 | Jones et al. |

FOREIGN PATENT DOCUMENTS

WO WO 2016/008433 A1 * 1/2016 ........... C07D 261/14

OTHER PUBLICATIONS

Oct. 12, 2018 International Search Report issued in International Patent Application No. PCT/CN2018/095241.
Oct. 12, 2018 Written Opinion of the International Searching Authority issued in International Patent Application No. PCT/CN2018/095241.

* cited by examiner

*Primary Examiner* — Brian J Davis
(74) *Attorney, Agent, or Firm* — Oliff PLC

(57) ABSTRACT

A salt of a substituted urea derivative of formula (I) and use thereof in the pharmaceutical field. Also, a pharmaceutical composition containing the salt or a combination thereof, and use of the salt or the pharmaceutical composition in the manufacture of a medicament for treating, remitting or preventing a disorder related to tyrosine kinase activity.

(I)

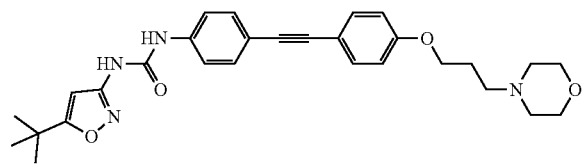

18 Claims, 14 Drawing Sheets

SALT OF SUBSTITUTED UREA DERIVATIVE AND USE THEREOF IN MEDICINE

CROSS-REFERENCE TO RELATED APPLICATION

This application claims priority to Chinese Patent Serial No. 201710569633.8, filed on Jul. 13, 2017, which is hereby incorporated by reference in its entirety.

FIELD OF THE INVENTION

The present invention belongs to the drug field, relates to a salt of a substituted urea derivative and use thereof, specifically to a salt of 1-(5-(tert-butyl)isoxazol-3-yl)-3-(4-((4-(3-morpholinopropoxy)phenyl)ethynyl)phenyl)urea (compound (I)) and use thereof, and further relates to a pharmaceutical composition containing the salt. The salt or the pharmaceutical composition thereof is used for treating, remitting or preventing a disorder related to tyrosine kinase activity.

BACKGROUND OF THE INVENTION

Aberrant or excessive activity or dysregulation of activity of receptor protein tyrosine kinase (RPTK) has been observed in many disease states including benign and malignant proliferative disorders as well as inflammatory disorders and immune system disorders that result from inappropriate activation of the immune system to cause, for example, autoimmune diseases. So far, there are about 58 kinds of receptor tyrosine kinases, including VEGF receptors, PDGF receptor (PDGF receptor (PDGFR) family is composed of five kinds of RTK composition: PDGFR-a and -b, CSFIR, c-KIT and FLT3), and FLK receptor family and so on. These receptors can transduce signals to other tyrosine kinases, such as SRC, RAF, FRK, BTK, CSK, ABI, FES/FPS, FAK, JAK, ACK, etc.

FLT3, a type III receptor tyrosine kinase, plays an important role in the proliferation and differentiation of hematopoietic stem cells, and activating mutation or overexpression of this receptor is found in AML (acute myeloid leukemia) (See, Heinrich, Mini-Reviews in Medicinal Chemistry, 2004, 4(3): 255-271, and Kiyoi et al., Int J Hematol., 2005, 82: 85-92, incorporated herein by reference). One study shows the FLT3 inhibtor CEP-701 may be effective in reducing myelin loss in experimental autoimmune encephalomyelitis (EAE), a mouse model for multiple sclerosis (See, Whartenby et al., PNAS, 2005, 102: 16741-16746, incorporated herein by reference). A high level of the FLT3 ligand is found in the serum of patients with Langerhans cell histiocytosis and systemic lupus erythematosus, that further means FLT3 signal transduction is implicated in the dysregulation of dendritic cell progenitors in those autoimmune diseases (See, Rolland et al., J. Immunol., 2005, 174:3067-3071, incorporated herein by reference).

Activating internal tandem duplication (ITD) mutations in FLT3 (FLT3-ITD) are detected in approximately 20% of acute myeloid leukemia patients and are associated with a poor prognosis. Research has shown that FLT3-ITD inhibitor plays a role in hindering inducing malignant tumor according to malignancy pathogenesis, and achieving valid therapeutic target in AML patient (See, Catherine et al., Nature, 2012, 485: 260-263, incorporated herein by reference). Mutation of FLT3 gene is a frequent event in AML patient and usually involves internal tandem duplication (ITD) of the juxtamembrane domain coding region or point mutations of the tyrosine kinase domain (TKD). Both FLT3-ITD and FLT3-TKD mutations result in ligand-independent proliferation due to constitutive dimerisation and activation of the FLT3 receptor. High mutant-to-wild type allelic ratios of FLT3-ITD are associated with a very poor prognosis in both adults and children (See, A S Moore et al., Leukemia, 2012, 26: 1462-1470, incorporated herein by reference). 1462-1470).

Bcr-ABL is a tyrosine kinase which inhibits cellular cancerization and immortalization of pH-positive chronic myeloid leukemia (CML) and acute lymphoblastic leukemia (ALL). bcr-Abl protein is the constitutively active, cytoplasmic tyrosine kinase existing in 90% of the patients of chronic myeloid leukemia and 15-30% of the adult patients of acute lymphoblastic leukemia. Many studies have shown that Bcr-ABL activation is the need of carcinogenic ability of said chimeric protein.

In recent years, the abnormalities of c-KIT gene, a member of type III receptor tyrosine kinase family in AML, have attracted more attentions. It was found that mutations of c-KIT gene will cause the activation of c-KIT without receptor-ligand binding, thereby the abnormal proliferation of cells occurs, leading to cancer. c-KIT gene mutation in leukemia cell is closely associated with the occurrence of leukemia and the prognosis of therapeutic agent. c-KIT receptor also can be constitutively activated by mutation, leading to abnormal cell proliferation and development, such as mastocytosis (D816V mutation) and other diseases, such as various cancers, e.g., GIST (c-KIT 427, juxtamembrane deletion).

Patent applications WO2016008433 and CN105272930 disclosed substituted urea derivatives having receptor tyrosine kinase inhibitory activity, wherein the compound with chemical name of 1-(5-(tert-butyl)isoxazol-3-yl)-3-(4-((4-(3-morpholinopropoxy)phenyl) ethynyl)phenyl)urea (compound (I)) can treat, remit or prevent a disease related to tyrosine kinase activity effectively.

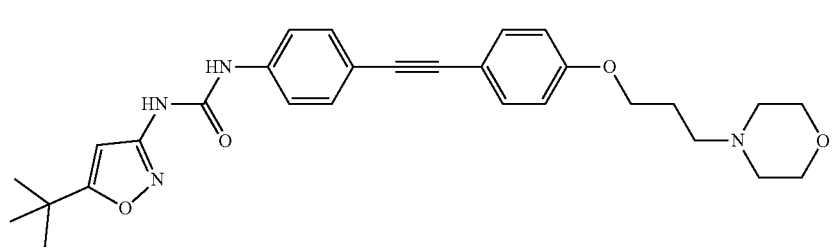

(I)

Drug polymorphism is a common phenomenon in drug research, it is an important factor affecting drug quality. Various crystalline forms of the same drug have significantly different appearance, solubility, melting point, dissolution, bioavailability, and so on, also have different effects on stability, bioavailability and efficacy of drug. Therefore, the polymorphism problem of a drug should be considered overall in drug research.

The pharmaceutically acceptable acid addition salt of compound (I) and composition disclosed herein have a better biological activity, and obviously improve the stability and pharmacokinetic properties of the compound, and have a better druggability.

The acid addition salt disclosed herein include a crystalline form, a part crystalline form, a polymorphism and a solvate thereof. The present invention further provides a crystalline form of a salt of compound (I) and a composition thereof, and use of them in the manufacture of a medicament for treating, remitting or preventing a disease related to tyrosine kinase activity.

SUMMARY OF THE INVENTION

Substituted urea derivative 1-(5-(tert-butyl)isoxazol-3-yl)-3-(4-((4-(3-morpholinopropoxy) phenyl)ethynyl)phenyl)urea (compound (I)) is a yellow alkaline solid, the present invention have studied on salts and cyrstalline forms thereof of compound (I) for improving the stability and bioavailability.

In particular, the present invention relates to an acid addition salt of compound (I) and a pharmaceutical composition thereof, and use of them in the manufacture of a medicament for treating, remitting, or preventing a disease related to tyrosine kinase activity. The acid addition salt disclosed herein includes a crystalline form, a part crystalline form, a polymorphism, an amorphism, a hydrate or a solvate.

In one aspect, the present invention provides a pharmaceutically acid addition salt of compound (I),

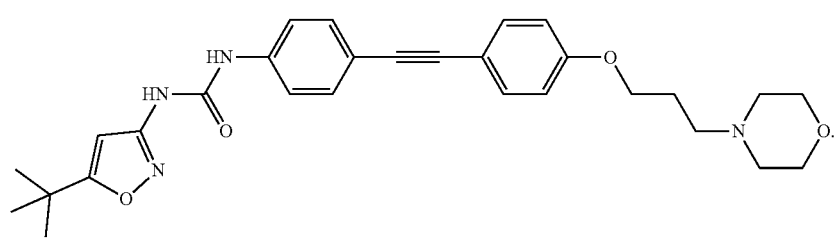

(I)

In some embodiments, the acid addition salt provided herein is an inorganic acid salt or organic acid salt.

In some embodiments, the inorganic acid salt provided herein is hydrochloride, sulfate, hydrosulfate, nitrate, hydrobromide, hydriodate, carbonate, bicarbonate, sulfite, bisulfite, pyrosulfate, hydrophosphate, dihydric phosphate, perchlorate, persulfate, hemisulphate, bisulphate, thiocyanate, phosphate, pyrophosphate, metaphosphate or a combination thereof.

In some embodiments, the organic acid salt provided herein is formate, acetate, propionate, butyrate, benzoate, malonate, succinate, pyruvate, ethanesulfonate, propanesulfonate, citrate, 4-nitrobenzoate, benzene sulfonate, tosilate, L-malate, mesylate, propiolate, 2-butynoate, vinyl acetate, L-tartrate, fumarate, lactate, lactobionate, pamoate, salicylate, galactarate, gluceptate, mandelate, 1,2-ethanedisulfonate, naphthalenesulfonate, β-naphthalenesulfonate, oxalate, maleate, tartrate, trifluoroacetate, trifluoromethanesulfonate, adipate, suberate, sebacate, butyne-1,4-dioate, hexene-1,6-dioate, hydroxyacetate, alginate, ascorbate, erythorbate, aspartate, glutamate, 2-phenoxybenzoate, 2-(4-hydroxybenzoyl)benzoate, acetoacetate, 2-hydroxyethanesulfonate, borate, chlorobenzoate, camphorate, itaconate, levocamphorsulfonate, methylbenzoate, dinitrobenzoate, sulfamate, digalacturonate, galacturonate, cyclopentylpropanoate, dodecyl sulfate, acrylate, cypionate, glycerophosphate, methoxybenzoate, digluconate, gluconate, heptylate, hexanoate, pivalate, glucuronate, laurate, phthalate, laurylsulfate, 2-acetoxybenzoate, nicotinate, cinnamate, oleate, palmitate, pamoate, pectate, benzenedicarboxylate, glutarate, hydroxymaleate, hydroxybenzoate, phenylacetate, 3-hydroxy-2-naphthoate, 3-phenylpropionate, isobutyrate, pivalate, picrate, stearate, 2.2-dichloroacetate, acylated amino-acid salt, alginate, 4-acetamidobenzene sulfonate, decanoate, cholate, caprylate, pelargonate, cyclamate, phthalate, cysteinate hydrochloride, sorbate, pamoate, mucate, glycinate hydrochloride, naphthalenedisulfonate, xylene sulfonate, cystinate dihydrochloride, undecanoate, poly(vinylsulfonate), sulfosalicylate, phenylbutyrate, 4-hydroxybutyrate, poly(vinylsulfate), naphthalene-1-sulfonate, naphthalene-2-sulfonate, valerate or a combination thereof.

In some embodiments, the salt provided herein is hydrobromide crystalline I, wherein hydrobromide crystalline I has an X-ray powder diffraction pattern comprising one or more peaks expressed as 2θ at 11.13°±0.2°, 20.74°±0.2°, 24.16°±0.2°, 25.65°±0.2°.

In some embodiments, the salt provided herein is hydrobromide crystalline I, wherein hydrobromide crystalline I has an X-ray powder diffraction pattern comprising one or more peaks expressed as 2θ at 11.13°±0.2°, 15.54°±0.2°, 16.40°±0.2°, 19.15°±0.2°, 19.74°±0.2°, 20.74°±0.2°, 22.83°±0.2°, 24.16°±0.2°, 25.65°±0.2°, 25.85°±0.2°.

In some embodiments, the salt provided herein is hydrobromide crystalline I, wherein hydrobromide crystalline I has an X-ray powder diffraction pattern comprising one or more peaks expressed as 2θ at 8.28°±0.2°, 11.13°±0.2°, 11.65°±0.2°, 11.88°±0.2°, 13.05°±0.2°, 15.02°±0.2°, 15.54°±0.2°, 15.90°±0.2°, 16.40°±0.2°, 16.57°±0.2°, 17.50°±0.2°, 18.09°±0.2°, 19.15°±0.2°, 19.74°±0.2°, 20.16°±0.2°, 20.74°±0.2°, 21.47°±0.2°, 21.81°±0.2°, 22.56°±0.2°, 22.83°±0.2°, 23.03°±0.2°, 23.20°±0.2°, 23.70°±0.2°, 24.16°±0.2°, 24.47°±0.2°, 25.03°±0.2°, 25.21°±0.2°, 25.65°±0.2°, 25.85°±0.2°, 26.50°±0.2°, 27.96°±0.2°, 28.43°±0.2°, 29.70°±0.2°, 30.26°±0.2°, 30.79°±0.2°, 31.44°±0.2°, 32.16°±0.2°, 33.57°±0.2°, 33.96°±0.2°, 34.68°±0.2°, 35.83°±0.2°, 36.89°±0.2°, 37.42°±0.2°, 38.23°±0.2°.

In some embodiments, hydrobromide crystalline I provided herein has an X-ray powder diffraction pattern substantially the same as shown in FIG. 1.

In some embodiments, hydrobromide crystalline I provided herein has a differential scanning calorimetry thermogram comprising an endothermic peak at 242.41° C.±3° C.

In some embodiments, hydrobromide crystalline I provided herein has a differential scanning calorimetry thermogram substantially the same as shown in FIG. 8.

In some embodiments, the salt provided herein is hydrochloride crystalline I, wherein hydrochloride crystalline I has an X-ray powder diffraction pattern comprising one or more peaks expressed as 2θ at 18.45°±0.2°, 19.14°±0.2°, 19.83°±0.2°, 21.70°±0.2°, 23.62°±0.2°.

In some embodiments, the salt provided herein is hydrochloride crystalline I, wherein hydrochloride crystalline I has an X-ray powder diffraction pattern comprising one or more peaks expressed as 2θ at 7.11°±0.2°, 14.26°±0.2°, 15.53°±0.2°, 16.21°±0.2°, 18.45°±0.2°, 19.14°±0.2°, 19.83°±0.2°, 21.70°±0.2°, 22.48°±0.2°, 23.62°±0.2°.

In some embodiments, the salt provided herein is hydrochloride crystalline I, wherein hydrochloride crystalline I has an X-ray powder diffraction pattern comprising one or more peaks expressed as 2θ at 6.63°±0.2°, 7.11°±0.2°, 8.53°±0.2°, 10.50°±0.2°, 12.76°±0.2°, 13.22°±0.2°, 14.26°±0.2°, 14.54°±0.2°, 15.53°±0.2°, 16.21°±0.2°, 16.63°±0.2°, 17.05°±0.2°, 17.41°±0.2°, 17.77°±0.2°, 18.45°±0.2°, 19.14°±0.2°, 19.83°±0.2°, 20.13°±0.2°, 21.15°±0.2°, 21.70°±0.2°, 22.48°±0.2°, 23.62°±0.2°, 23.97°±0.2°, 24.77°±0.2°, 25.37°±0.2°, 26.01°±0.2°, 27.15°±0.2°, 27.84°±0.2°, 29.57°±0.2°, 31.29°±0.2°, 32.54°±0.2°, 33.38°±0.2°, 35.19°±0.2°, 36.27°±0.2°.

In some embodiments, hydrochloride crystalline I provided herein has an X-ray powder diffraction pattern substantially the same as shown in FIG. 2.

In some embodiments, hydrochloride crystalline I provided herein has a differential scanning calorimetry thermogram comprising an endothermic peak at 258.45° C.±3° C.

In some embodiments, hydrochloride crystalline I provided herein has a differential scanning calorimetry thermogram substantially the same as shown in FIG. 9.

In some embodiments, the salt provided herein is benzene sulfonate crystalline I, wherein benzene sulfonate crystalline I has an X-ray powder diffraction pattern comprising one or more peaks expressed as 2θ at 6.74°±0.2°, 17.30°±0.2°, 18.98°±0.2°, 22.27°±0.2°, 22.64°±0.2°.

In some embodiments, the salt provided herein is benzene sulfonate crystalline I, wherein benzene sulfonate crystalline I has an X-ray powder diffraction pattern comprising one or more peaks expressed as 2θ at 6.74°±0.2°, 10.95°±0.2°, 17.30°±0.2°, 18.98°±0.2°, 21.56°±0.2°, 21.91°±0.2°, 22.27°±0.2°, 22.64°±0.2°, 23.23°±0.2°, 23.89°±0.2°.

In some embodiments, the salt provided herein is benzene sulfonate crystalline I, wherein benzene sulfonate crystalline I has an X-ray powder diffraction pattern comprising one or more peaks expressed as 2θ at 6.74°±0.2°, 7.16°±0.2°, 10.95°±0.2°, 13.54°±0.2°, 14.33°±0.2°, 15.78°±0.2°, 16.46°±0.2°, 16.74°±0.2°, 17.30°±0.2°, 17.82°±0.2°, 18.20°±0.2°, 18.46°±0.2°, 18.69°±0.2°, 18.98°±0.2°, 19.21°±0.2°, 19.47°±0.2°, 19.72°±0.2°, 20.14°±0.2°, 20.49°±0.2°, 20.98°±0.2°, 21.56°±0.2°, 21.91°±0.2°, 22.27°±0.2°, 22.64°±0.2°, 23.23°±0.2°, 23.89°±0.2°, 24.45°±0.2°, 24.60°±0.2°, 25.46°±0.2°, 26.28°±0.2°, 26.53°±0.2°, 26.98°±0.2°, 27.30°±0.2°, 27.71°±0.2°, 28.38°±0.2°, 29.09°±0.2°, 29.47°±0.2°, 30.11°±0.2°, 30.74°±0.2°, 31.28°±0.2°, 31.54°±0.2°, 33.26°±0.2°, 33.85°±0.2°, 34.60°±0.2°, 35.36°±0.2°, 35.74°±0.2°, 36.69°±0.2°.

In some embodiments, the salt provided herein is benzene sulfonate crystalline I, wherein benzene sulfonate crystalline I has an X-ray powder diffraction pattern substantially the same as shown in FIG. 3.

In some embodiments, the salt provided herein is benzene sulfonate crystalline I, wherein benzene sulfonate crystalline I has a differential scanning calorimetry thermogram comprising an endothermic peak at 189.55° C.±3° C.

In some embodiments, the acid addition salt provided herein is benzene sulfonate crystalline I, wherein benzene sulfonate crystalline I has a differential scanning calorimetry thermogram substantially the same as shown in FIG. 10.

In some embodiments, the salt provided herein is benzene sulfonate crystalline II, wherein benzene sulfonate crystalline II has an X-ray powder diffraction pattern comprising one or more peaks expressed as 2θ at 6.14°±0.2°, 17.10°±0.2°, 18.23°±0.2°, 21.63°±0.2°, 22.49°±0.2°.

In some embodiments, the salt provided herein is benzene sulfonate crystalline II, wherein benzene sulfonate crystalline II has an X-ray powder diffraction pattern comprising one or more peaks expressed as 2θ at 6.14°±0.2°, 9.22°±0.2°, 17.10°±0.2°, 17.49°±0.2°, 18.23°±0.2°, 19.57°±0.2°, 20.18°±0.2°, 21.23°±0.2°, 21.63°±0.2°, 22.49°±0.2°.

In some embodiments, the salt provided herein is benzene sulfonate crystalline II, wherein benzene sulfonate crystalline II has an X-ray powder diffraction pattern comprising one or more peaks expressed as 2θ at 6.14°±0.2°, 6.66°±0.2°, 9.22°±0.2°, 12.31°±0.2°, 12.97°±0.2°, 15.33°±0.2°, 16.17°±0.2°, 16.48°±0.2°, 17.10°±0.2°, 17.49°±0.2°, 18.23°±0.2°, 18.53°±0.2°, 19.57°±0.2°, 20.18°±0.2°, 21.23°±0.2°, 21.63°±0.2°, 22.49°±0.2°, 23.69°±0.2°, 24.18°±0.2°, 24.66°±0.2°, 25.52°±0.2°, 26.46°±0.2°, 27.78°±0.2°, 28.34°±0.2°, 29.15°±0.2°, 30.64°±0.2°, 30.99°±0.2°, 32.45°±0.2°, 33.93°±0.2°, 34.70°±0.2°, 35.48°±0.2°, 38.57°±0.2°.

In some embodiments, benzene sulfonate crystalline II provided herein has a differential scanning calorimetry thermogram comprising endothermic peaks at 167.42° C.±3° C. and 173.39° C.±3° C.

In some embodiments, benzene sulfonate crystalline II provided herein has an X-ray powder diffraction pattern substantially the same as shown in FIG. 4.

In some embodiments, benzene sulfonate crystalline II provided herein has a differential scanning calorimetry thermogram substantially the same as shown in FIG. 11.

In some embodiments, the salt provided herein is benzene sulfonate crystalline III, wherein benzene sulfonate crystalline III has an X-ray powder diffraction pattern comprising one or more peaks expressed as 2θ at 6.12°±0.2°, 16.93°±0.2°, 17.92°±0.2°, 21.67°±0.2°, 22.60°±0.2°.

In some embodiments, benzene sulfonate crystalline III provided herein has an X-ray powder diffraction pattern comprising one or more peaks expressed as 2θ at 6.12°±0.2°, 15.33°±0.2°, 16.93°±0.2°, 17.92°±0.2°, 18.21°±0.2°, 18.46°±0.2°, 20.29°±0.2°, 21.38°±0.2°, 21.67°±0.2°, 22.60°±0.2°, 22.99°±0.2°.

In some embodiments, benzene sulfonate crystalline III provided herein has an X-ray powder diffraction pattern comprising one or more peaks expressed as 2θ at 6.12°±0.2°, 6.61°±0.2°, 11.36°±0.2°, 11.89°±0.2°, 12.31°±0.2°, 12.72°±0.2°, 12.95°±0.2°, 13.17°±0.2°, 13.71°±0.2°, 14.64°±0.2°, 15.33°±0.2°, 16.49°±0.2°, 16.93°±0.2°, 17.11°±0.2°, 17.92°±0.2°, 18.21°±0.2°, 18.46°±0.2°, 19.49°±0.2°, 20.29°±0.2°, 21.38°±0.2°, 21.67°±0.2°, 22.60°±0.2°, 22.99°±0.2°, 24.10°±0.2°, 24.37°±0.2°, 24.89°±0.2°, 25.61°±0.2°, 26.52°±0.2°, 27.63°±0.2°, 28.03°±0.2°, 29.07°±0.2°, 29.49°±0.2°, 30.22°±0.2°, 30.92°±0.2°, 31.16°±0.2°, 32.55°±0.2°, 33.53°±0.2°, 34.96°±0.2°, 37.51°±0.2°, 38.94°±0.2°.

In some embodiments, benzene sulfonate crystalline III provided herein has a differential scanning calorimetry thermogram comprising an endothermic peak at 139.64° C.±3° C.

In some embodiments, benzene sulfonate crystalline III provided herein has an X-ray powder diffraction pattern substantially the same as shown in FIG. 5.

In some embodiments, benzene sulfonate crystalline III provided herein has a differential scanning calorimetry thermogram substantially the same as shown in FIG. 12.

In some embodiments, the salt provided herein is benzene sulfonate crystalline IV, wherein benzene sulfonate crystalline IV has an X-ray powder diffraction pattern comprising one or more peaks expressed as 2θ at 17.01°±0.2°, 18.08°±0.2°, 21.10°±0.2°, 22.47°±0.2°, 22.77°±0.2°.

In some embodiments, benzene sulfonate crystalline IV provided herein has an X-ray powder diffraction pattern comprising one or more peaks expressed as 2θ at 16.42°±0.2°, 17.01°±0.2°, 18.08°±0.2°, 18.31°±0.2°, 19.34°±0.2°, 20.05°±0.2°, 21.10°±0.2°, 22.47°±0.2°, 22.77°±0.2°, 27.75°±0.2°.

In some embodiments, benzene sulfonate crystalline IV provided herein has an X-ray powder diffraction pattern comprising one or more peaks expressed as 2θ at 6.07°±0.2°, 9.15°±0.2°, 11.28°±0.2°, 12.22°±0.2°, 12.47°±0.2°, 12.85°±0.2°, 13.71°±0.2°, 14.36°±0.2°, 15.21°±0.2°, 15.67°±0.2°, 16.11°±0.2°, 16.42°±0.2°, 17.01°±0.2°, 17.38°±0.2°, 17.84°±0.2°, 18.08°±0.2°, 18.31°±0.2°, 19.34°±0.2°, 19.47°±0.2°, 19.69°±0.2°, 20.05°±0.2°, 21.10°±0.2°, 21.56°±0.2°, 21.80°±0.2°, 22.47°±0.2°, 22.77°±0.2°, 23.14°±0.2°, 23.68°±0.2°, 24.01°±0.2°, 24.29°±0.2°, 24.62°±0.2°, 25.34°±0.2°, 26.01°±0.2°, 26.36°±0.2°, 26.96°±0.2°, 27.48°±0.2°, 27.75°±0.2°, 28.23°±0.2°, 28.45°±0.2°, 29.06°±0.2°, 29.18°±0.2°, 29.40°±0.2°, 29.74°±0.2°, 30.48°±0.2°, 30.64°±0.2°, 31.07°±0.2°, 31.61°±0.2°, 32.56°±0.2°, 33.16°±0.2°, 33.44°±0.2°.

In some embodiments, benzene sulfonate crystalline IV provided herein has a differential scanning calorimetry thermogram comprising endothermic peaks at 160.59° C.±3° C. and 203.47° C.±3° C.

In some embodiments, benzene sulfonate crystalline IV provided herein has an X-ray powder diffraction pattern substantially the same as shown in FIG. 6.

In some embodiments, benzene sulfonate crystalline IV provided herein has a differential scanning calorimetry thermogram substantially the same as shown in FIG. 13.

In some embodiments, the salt provided herein is benzene sulfonate crystalline V, wherein benzene sulfonate crystalline V has an X-ray powder diffraction pattern comprising one or more peaks expressed as 2θ at 6.49°±0.2°, 17.28°±0.2°, 18.50°±0.2°, 19.57°±0.2°, 23.60°±0.2°.

In some embodiments, benzene sulfonate crystalline V provided herein has an X-ray powder diffraction pattern comprising one or more peaks expressed as 2θ at 6.49°±0.2°, 17.28°±0.2°, 18.50°±0.2°, 19.57°±0.2°, 20.16°±0.2°, 21.66°±0.2°, 22.24°±0.2°, 22.60°±0.2°, 23.13°±0.2°, 23.60°±0.2°.

In some embodiments, benzene sulfonate crystalline V provided herein has an X-ray powder diffraction pattern comprising one or more peaks expressed as 2θ at 6.49°±0.2°, 9.62°±0.2°, 12.08°±0.2°, 13.04°±0.2°, 14.22°±0.2°, 14.60°±0.2°, 14.87°±0.2°, 15.90°±0.2°, 16.33°±0.2°, 16.66°±0.2°, 17.28°±0.2°, 18.18°±0.2°, 18.50°±0.2°, 19.57°±0.2°, 20.16°±0.2°, 20.89°±0.2°, 21.66°±0.2°, 22.24°±0.2°, 22.60°±0.2°, 23.13°±0.2°, 23.60°±0.2°, 24.09°±0.2°, 24.33°±0.2°, 24.55°±0.2°, 25.17°±0.2°, 26.17°±0.2°, 27.08°±0.2°, 27.50°±0.2°, 28.73°±0.2°, 29.09°±0.2°, 29.62°±0.2°, 30.50°±0.2°, 31.62°±0.2°, 32.71°±0.2°, 33.87°±0.2°, 34.62°±0.2°, 36.64°±0.2°, 37.46°±0.2°, 38.22°±0.2°, 39.94°±0.2°.

In some embodiments, benzene sulfonate crystalline V provided herein has an X-ray powder diffraction pattern substantially the same as shown in FIG. 7.

In some embodiments, benzene sulfonate crystalline V provided herein has a differential scanning calorimetry thermogram substantially the same as shown in FIG. 14.

In some embodiments, benzene sulfonate crystalline V provided herein has a differential scanning calorimetry thermogram comprising an endothermic peak at 202.15° C.±3° C.

In other aspect, the present invention also provides a pharmaceutical composition comprising any one acid addition salt of compound (I) or a combination thereof.

In some embodiments, the pharmaceutical composition disclosed herein further comprises a pharmaceutically acceptable carrier, excipient, diluent, adjuvant or a combination thereof.

In some embodiments, the pharmaceutical composition disclosed herein further comprises other active agent used for treating proliferative diseases, autoimmune diseases or inflammatory diseases, wherein the other active agent is chemotherapeutic drug, antiproliferative agent, immunosuppressor, immunologic stimulant, anti-inflammatory reagent, agent for treating atherosclerosis, agent for treating pulmonary fibrosis, CDK4/6 kinase inhibitor, ABL inhibitor, ABL/Scr inhibitor, aurora kinase inhibitor, non-ATP competitive inhibitor of BCR-ABL, c-KIT mutation inhibitor, RET inhibitor, PDGFR inhibitor, VEGFR inhibitor, FLT3 inhibitor, FLT3-ITD inhibitor or a combination thereof.

In some embodiments, the pharmaceutical composition disclosed herein further comprises other active agent used for treating proliferative diseases, autoimmune diseases or inflammatory diseases, wherein the other active agent is chlorambucil, melphalan, cyclophosphamide, ifosfamide, busulfan, carmustine, lomustine, streptozotocin, cis-platinum, carboplatin, oxaliplatin, dacarbazine, temozolomide, procarbozine, methotrexate, fluorouracil, cytosine arabinoside, gemcitabine, purinethol, fludarabine, vinblastine, vincristine, vinorelbine, paclitaxel, docetaxel, topotecan, irinotecan, etoposide, trabectedin, dactinomycin, doxorubicin, pharmorubicin, daunomycin, mitoxantrone, bleomycin, mitomycin C, ixabepilone, tamoxifen, flutamide, gonadorelin analogue, megestrol acetate, prednisone, dexamethasone, methylprednisolone, thalidomide, interferon α, calcium folinate, sirolimus, temsirolimus, everolimus, afatinib, alisertib, amuvatinib, apatinib, axitinib, bortezomib, bosutinib, brivanib, cabozantinib, cediranib, crenolanib, crizotinib, dabrafenib, dacomitinib, danusertib, dasatinib, dovitinib, erlotinib, foretinib, ganetespib, gefitinib, ibrutinib, icotinib, imatinib, iniparib, lapatinib, lenvatinib, linifanib, linsitinib, masitinib, momelotinib, motesanib, neratinib, nilotinib, niraparib, oprozomib, olaparib, pazopanib, pictilisib, ponatinib, quizartinib, regorafenib, rigosertib, rucaparib, ruxolitinib, saracatinib, saridegib, sorafenib, sunitinib, tasocitinib, telatinib, tivantinib, tivozanib, tofacitinib, trametinib, vandetanib, veliparib, zelboraf, vismodegib, volasertib, alemtuzumab, bevacizumab, brentuximab vedotin, catumaxomab, cetuximab, denosumab, gemtuzumab, ipilimumab, nimotuzumab, ofatumumab, panitumumab, rituximab, tositumomab, trastuzumab, cabozantinib, ponatinib, midostaurin, pacritinib, gilteritinib, AKN-028, AT-9283, crenolanib, ENMD-2076, famitinib, dovitinib, PLX-3397, palbociclib, abemaciclib, ribociclib, rigosertib sodium, selinexor, roniciclib, AT-7519, seliciclib, alvocidib or a combination thereof.

In other aspect, the present invention provides use of the acid addition salt or a combination thereof or the pharmaceutical composition in the manufacture a medicament for preventing, managing, treating, remitting or lessening proliferative diseases, autoimmune diseases or inflammatory diseases in a patient.

In some embodiments, the proliferative disease is chronic myelogenous leukemia, gastrointestinal stromal tumor, acute myelocytic leukemia (AML), mutated chronic myeloid leukemia (CML), acute lymphoblastic leukemia (ALL), leukaemia, chronic lymphocytic leukemia, primary macroglobulinemia, monocytic leukemia, leukemoid reaction, aplastic anemia, hemacelinosis, secondary or benign monoclonal gammopathy, semi molecular disease, colorectal cancer, gastric cancer, mammary cancer, lung cancer, liver cancer, prostatic cancer, pancreatic cancer, cancerous goiter, renal carcinoma, cerebroma, neck cancer, central nervous system cancer, malignant glioma, myeloproliferative disease, infectious mononucleosis, malignant histiocytosis, lymphoma, non lymphoreticular system tumor, multiple myeloma, granulocytic sarcoma, solitary plasmacytoma, malignant lymphoma, osteolytic lesion, lymphoblastoma, non-Hodgkin lymphoma, infectious mononucleosis, acute histiocytosis, Hodgkin's lymphoma, colon cancer, rectal cancer, small cell lung cancer, neuroblastoma, neuroendocrine cell tumor, islet cell tumor, medullary thyroid carcinoma, melanoma, retinoblastoma, uterine cancer, ovarian cancer, head and neck squamous cell carcinoma, alimentary canal malignancy, non-small cell lung cancer, cervical cancer, testiculoma, bladder cancer, myeloma or complications related to AML.

In other embodiments, the autoimmune disease is leukaemia, chronic myelogenous leukemia, gastrointestinal stromal tumor, acute myelocytic leukemia (AML), mutated chronic myeloid leukemia (CML), acute lymphoblastic leukemia (ALL), rheumatic arthritis, osteoarthralgia, central nervous system involvement, lupus, multiple sclerosis, thyroiditis, type I diabetes, sarcoidosis, inflammatory bowel disease, Crohn's disease, systemic lupus or complications related to acute myelocytic leukemia (AML);

In still other embodiments, the inflammatory disease is diverticulitis, colitis, pancreatitis, hepatitis, chronic hepatitis, cirrhosis, cholecystitis or chronic inflammation.

In other embodiments, the disease is caused by mutation of c-KIT or mediation of RET, PDGFR, VEGFR, Bcr-ABL, FLT3 or FLT3-ITD.

In another aspect, provided herein is a method of preventing, managing, treating, remitting or lessening proliferative diseases, autoimmune diseases or inflammatory diseases in a patient comprising administering the acid addition salt disclosed herein or a combination thereof or the pharmaceutical composition disclosed herein to the patient.

In some embodiments, the proliferative disease is chronic myelogenous leukemia, gastrointestinal stromal tumor, acute myelocytic leukemia, mutated chronic myeloid leukemia, acute lymphoblastic leukemia, leukaemia, chronic lymphocytic leukemia, primary macroglobulinemia, monocytic leukemia, leukemoid reaction, aplastic anemia, hemacelinosis, secondary or benign monoclonal gammopathy, semi molecular disease, colorectal cancer, gastric cancer, mammary cancer, lung cancer, liver cancer, prostatic cancer, pancreatic cancer, cancerous goiter, renal carcinoma, cerebroma, neck cancer, central nervous system cancer, malignant glioma, myeloproliferative disease, infectious mononucleosis, malignant histiocytosis, lymphoma, non lymphoreticular system tumor, multiple myeloma, granulocytic sarcoma, solitary plasmacytoma, malignant lymphoma, osteolytic lesion, lymphoblastoma, non-Hodgkin lymphoma, infectious mononucleosis, acute histiocytosis, Hodgkin's lymphoma, colon cancer, rectal cancer, small cell lung cancer, neuroblastoma, neuroendocrine cell tumor, islet cell tumor, medullary thyroid carcinoma, melanoma, retinoblastoma, uterine cancer, ovarian cancer, head and neck squamous cell carcinoma, alimentary canal malignancy, non-small cell lung cancer, cervical cancer, testiculoma, bladder cancer, myeloma or complications related to acute myelocytic leukemia;

the autoimmune disease is leukaemia, chronic myelogenous leukemia, gastrointestinal stromal tumor, acute myelocytic leukemia, mutated chronic myeloid leukemia, acute lymphoblastic leukemia, rheumatic arthritis, osteoarthralgia, central nervous system involvement, lupus, multiple sclerosis, thyroiditis, type I diabetes, sarcoidosis, inflammatory bowel disease, Crohn's disease, systemic lupus or complications related to acute myelocytic leukemia;

the inflammatory disease is diverticulitis, colitis, pancreatitis, hepatitis, chronic hepatitis, cirrhosis, cholecystitis or chronic inflammation.

In other embodiments, the medicament is used for preventing, managing, treating, remitting or lessening a disease caused by mutation of c-KIT or mediation of RET, PDGFR, VEGFR, Bcr-ABL, FLT3 or FLT3-ITD in a patient.

In another aspect, provided herein is the acid addition salt disclosed herein or a combination thereof or the pharmaceutical composition disclosed herein for use in preventing, managing, treating, remitting or lessening proliferative diseases, autoimmune diseases or inflammatory diseases in a patient.

In some embodiments, the proliferative disease is chronic myelogenous leukemia, gastrointestinal stromal tumor, acute myelocytic leukemia, mutated chronic myeloid leukemia, acute lymphoblastic leukemia, leukaemia, chronic lymphocytic leukemia, primary macroglobulinemia, monocytic leukemia, leukemoid reaction, aplastic anemia, hemacelinosis, secondary or benign monoclonal gammopathy, semi molecular disease, colorectal cancer, gastric cancer, mammary cancer, lung cancer, liver cancer, prostatic cancer, pancreatic cancer, cancerous goiter, renal carcinoma, cerebroma, neck cancer, central nervous system cancer, malignant glioma, myeloproliferative disease, infectious mononucleosis, malignant histiocytosis, lymphoma, non lymphoreticular system tumor, multiple myeloma, granulocytic sarcoma, solitary plasmacytoma, malignant lymphoma, osteolytic lesion, lymphoblastoma, non-Hodgkin lymphoma, infectious mononucleosis, acute histiocytosis, Hodgkin's lymphoma, colon cancer, rectal cancer, small cell lung cancer, neuroblastoma, neuroendocrine cell tumor, islet cell tumor, medullary thyroid carcinoma, melanoma, retinoblastoma, uterine cancer, ovarian cancer, head and neck squamous cell carcinoma, alimentary canal malignancy, non-small cell lung cancer, cervical cancer, testiculoma, bladder cancer, myeloma or complications related to acute myelocytic leukemia;

the autoimmune disease is leukaemia, chronic myelogenous leukemia, gastrointestinal stromal tumor, acute myelocytic leukemia, mutated chronic myeloid leukemia, acute lymphoblastic leukemia, rheumatic arthritis, osteoarthralgia, central nervous system involvement, lupus, multiple sclerosis, thyroiditis, type I diabetes, sarcoidosis, inflammatory bowel disease, Crohn's disease, systemic lupus or complications related to acute myelocytic leukemia;

the inflammatory disease is diverticulitis, colitis, pancreatitis, hepatitis, chronic hepatitis, cirrhosis, cholecystitis or chronic inflammation.

In some embodiments, the medicament is used for preventing, managing, treating, remitting or lessening a disease caused by mutation of c-KIT or mediation of RET, PDGFR, VEGFR, Bcr-ABL, FLT3 or FLT3-ITD in a patient.

In other aspect, provided herein is a drug combination comprising the acid addition salt of compound (I) or the pharmaceutical composition and one or more other active agents used for treating proliferative diseases, autoimmune diseases or inflammatory diseases.

In some embodiments, the other activity agent comprises chemotherapeutic drug, antiproliferative agent, immunosuppressor, immunologic stimulant, anti-inflammatory agent, CDK4/6 kinase inhibitor, ABL inhibitor, ABL/Scr inhibitor, aurora kinase inhibitor, non-ATP competitive inhibitor of BCR-ABL, c-KIT mutation inhibitor, RET inhibitor, PDGFR inhibitor, VEGFR inhibitor, FLT3 inhibitor, FLT3-ITD inhibitor or a combination thereof.

In still other aspect, the present invention also relates to a method of preparing the acid addition salt of compound (I) provided herein and a crystalline form thereof.

The solvent used in the method for preparing the salt provided herein is not particularly restricted, any solvent is contained in the invention so long as it can dissolve the raw materials to a certain extent and don't impact its properties. Additionally, many similar modifications, or equivalent alternatives in the art, or solvent, solvent composition and the solvent composition with different proportions which are equivalent to those described in the invention, all are deemed to be included in the present invention. The optimal solvents used in any reaction step are provided herein.

The preparation experiment of the salt provided herein would be detailed in examples. Meanwhile, the present invention provides an activity test (such as pharmacokinetics test), solubility test, stability test and hygroscopicity test, etc. of the salt. It can be known from the results that the salts provided herein have a better biological activity, good solubility, high stability, and which are suitable for pharmacy.

In the drug hygroscopicity test of the salt disclosed herein, the feature description of hygroscopicity and definition of weight gain of hygroscopicity (Chinese Pharmacopoeia 2015 edition appendix 9103 drug hygroscopicity guiding principles, experimental conditions: 25° C.±1° C., 80%±2% relative humidity) are described as followed table:

The feature description of hygroscopicity and definition of weight gain of hygroscopicity

| Hygroscopicity characteristics | Weight gain of hygroscopicity |
|---|---|
| deliquescence | absorbing enough water and forming liquid |
| very hygroscopicity | no less than 15% |
| hygroscopicity | less than 15% but no less than 2% |
| slightly hygroscopicity | less than 2% but no less than 0.2% |
| No or almost no hygroscopicity | less than 0.2% |

The salt provided herein is not easy to be influenced by high humidity to deliquesce, the property is convenience for long period storage.

Definitions and General Terminology

Unless otherwise defined, all technical and scientific terms used herein have the same meaning as commonly understood by one of ordinary skill in the art to which this invention belongs. All patents and publications referred to herein are incorporated by reference in their entirety. Although any methods and materials similar or equivalent to those described herein can be used in the practice or testing of the present invention, the preferred methods, devices, and materials are now described.

"Pharmaceutically acceptable acid addition salt" refers to a salt formed from compound (I) of the invention and pharmaceutically acceptable nontoxic acid, including but not limited to various organic acid salts and inorganic acid salts described herein.

"Acid addition salt of the compound (I)" refers to a salt formed from compound (I) (free base) and various suitable organic acid or inorganic acid, includes, but is not limited to: hydrochloride, sulfate, hydrosulfate, nitrate, hydrobromide, hydriodate, carbonate, hydrocarbonate, sulphite, hydrosulphite, pyrosulfate, monohydric phosphate, dihydric phosphate, perchlorate, persulfate, hemisulphate, bisulphate, thiocyanate, phosphate, pyrophosphate, metaphosphate, formate, acetate, propionate, butyrate, benzoate, malonate, succinate, pyruvate, esilate, propanesulfonate, 4-nitrobenzoate, benzene sulfonate, tosilate, malate, propiolate, 2-butynate, vinyl acetate, tartrate, L-tartrate, fumarate, lactate, lactobionate, mesylate, β-naphthalenesulfonate, maleate, tartrate, pamoate, salicylate, galactarate, gluceptate, mandelate, 1,2-ethanedisulfonate, naphthalenesulfonate, oxalate, trifluoroacetates, trifluoromethanesulfonate, adipate, suberate, sebacate, butyne-1,4-dicarboxylate, hexyne-1,6-dicarboxylate, glycollate, alginate, ascorbate, erythorbate, aspartate, glutamate, 2-phenoxybenzoate, 2-(4-hydroxybenzoyl)benzoate, acetoacetate, 2-hydroxy-ethanesulfonate, borate, chlorobenzoate, camphorate, itaconate, levocamphorsulfonate, toluate, dinitrobenzoate, sulfamate, lactobionate, galacturonate, cyclopentylpropionate, dodecylsulfate, acrylate, cypionate, glycerophosphate, methoxybenzoate, digluconate, gluconate, enantate, caproate, pivalate, glucuronate, laurate, phthalate, lauryl sulfate, 2-acetoxybenzoate, nicotinate, cinnamate, oleate, palmitate, pamoate, pectate, phthalate, glutarate, hydroxymaleate, hydroxybenzoate, phenylacetate, 3-hydroxy-2-naphthoate, 3-phenylpropionate, isobutyrate, pivalate, picrate, stearate, 2,2-dichloroacetate, acylated amino-acid salt, alginate, 4-acetamidobenzenesulfonate, decanoate, cholate, caprylate, pelargonate, cyclamate, phthalate, cysteine hydrochloride, sorbate, pamote, mucate, glycine hydrochloride, naphthalenedisulfonate, xylene sulfonate, cystamine dihydrochloride, undecanoate, polyvinylsulfonate, sulfosalicylate, phenylbutyrate, 4-hydroxybutyrate, polyvinylsulfate, 1-naphthalenesulfonate, 2-naphthalenesulfonate or valerate, and so on. Wherein the "acid addition salt of the compound (I)" includes amorphous form or crystalline form, solvate, hydrate, and also includes polymorphism of the salt. For example, hydrochloride of compound (I) includes amorphous form, various crystalline forms, various solvates, various hydrates, and also polymorphism of the salt.

"Crystalline" or "crystal form" refers to a solid having a highly regular chemical structure, includes, but is not limited to, single- and multiple-component crystals, and/or polymorphic form of compound, solvate, hydrate, clathrate, cocrystal, salt, solvate of salt, hydrate of salt. Crystalline forms of a substance can be obtained by a number of methods, as known in the art. Such methods include, but are not limited to, melt crystallization, melt cooling, solvent crystallization, crystallization in confined spaces such as, e.g., in nanopores or capillaries, crystallization on surfaces or templates such as, e.g., on polymers, crystallization in the presence of additives, such as, e.g., co-crystal counter-molecules, desolvation, dehydration, rapid evaporation, rapid cooling, slow cooling, vapor diffusion, sublimation, reaction crystallization, antisolvent addition, grinding and solvent-drop grinding.

"Amorphism" or "amorphous form" refers to substance forming by particle (such as molecule, atom, ion) arranged in no periodic in three-dimensional space, which is characterized by a diffused X-ray powder diffraction pattern with no sharp peaks. Amorphism is a special physical form of solid substance, the ordered structural characteristics in a part of amorphous substance imply there are innumerable links between amorphous substance and crystal substance. Amorphous substance can be obtained through many methods as known in the art. These methods include, but are not limited to, rapid freezing method, anti-solvent flocculence method, ball-milling method, spray drying method, freeze-drying method, wet granulating method and solid dispersion technique, and the like.

The term "solvent" means a substance, typically a liquid, that is capable of completely or partially dissolving another substance, typically a solid. "Solvent" as used herein, includes but is not limited to water, acetic acid, acetone, acetonitrile, benzene, chloroform, carbon tetrachloride, dichloromethane, dimethylsulfoxide, 1,4-dioxane, ethanol, ethyl acetate, butanol, tert-butanol, N,N-dimethylacetamide, N,N-dimethylformamide, formamide, formic acid, heptane, hexane, isopropanol, methanol, methyl ethyl ketone, 1-methyl-2-pyrrolidinone, mesitylene, nitromethane, polyethylene glycol, propanol, 2-propanone, pyridine, tetrahydrofuran, toluene, xylene, mixtures thereof and the like.

The term "anti-solvent" refers to a fluid which promotes precipitation from the solvent of the product (or a precursor for the product). The anti-solvent may comprise a cold gas, or a fluid promoting the precipitation via a chemical reaction, or a fluid which decreases the solubility of the product in the solvent; it may be the same liquid as the solvent but at a different temperature or it may be a liquid which is different from the solvent.

The term "solvate," as used herein, means having on a surface, in a lattice or on a surface and in a lattice, solvents for the practice of the invention include, but are not limited to, water, acetic acid, acetone, acetonitrile, benzene, chloroform, tetrachloromethane, dichloromethane, dimethyl sulfoxide, 1,4-dioxane, ethanol, ethyl acetate, butanol, tert-butanol, N,N-dimethylacetamide, N,N-dimethylformamide, formamide, formic acid, heptane, hexane, isopropanol, methanol, methyl ethyl ketone, methylpyrrolidone, mesitylene, nitromethane, polyethylene glycol, propanol, pyridine, tetrahydrofuran, toluene, xylene, mixtures thereof etc. A specific example of a solvate is a hydrate, wherein the solvent on the surface, in the lattice or on the surface and in the lattice, is water. Hydrates may or may not have solvents other than water on the surface, in the lattice or on the surface and in the lattice of a substance.

Crystalline form or amorphism can be identified through multiple technological means, such as X-ray powder diffraction (XRPD), infrared spectroscopy (IR), melting point method, differential scanning calorimetry (DSC), thermogravimetry analysis (TGA), nuclear magnetic resonance method, Raman spectroscopy, X-ray single crystal diffraction, solution calorimetry, scanning electron microscope (SEM), quantitative analysis, solubility, dissolution velocity, etc.

Some informations such as change in crystalline form, crystallinity, crystal structure state, etc., can be obtained through detection by X-ray powder diffraction which is a common method used for identifying crystalline form. The peak position of XRPD pattern mainly depends on the crystal structure, which is relatively insensitive to experimental details, and the relative peak height depends on many factors related to sample preparation and the geometry of the instrument. Thus, in some embodiments, the crystalline form disclosed herein is characterized by an X-ray powder diffraction pattern having some peaks in certain positions, which is substantially the same as the XRPD pattern provided in appended figures of the present invention. Meanwhile, the measurement of $2\theta$ in XRPD pattern could have some experimental errors, for example the measurements of $2\theta$ in XRPD pattern could be slightly different because of different instruments and different samples. Therefore, the value of $2\theta$ is not absolute. According to the state of the instrument for the experiment disclosed herein, the error margin in $2\theta$ of the characteristic peaks is $\pm 0.2°$.

Differential scanning calorimetry (DSC) is a technology used for measuring the energy difference between a sample and a inert reference compound (usually $\alpha$-$Al_2O_3$) as a function of temperature, which is performed through constant heating or cooling under program control. The melting peak height of DSC thermogram depends on many factors related to sample preparation and the geometry of the instrument, and the peak position is relatively insensitive to experimental details. Thus, in some embodiments, the crystalline form disclosed herein is characterized by a DSC thermogram having some peaks in certain positions, which is substantially the same as the DSC thermogram provided in appended figures of the present invention. Meanwhile, a DSC thermogram could have some experimental errors, for example the peak position and the peak value in the DSC thermogram could be slightly different because of different instruments and different samples. Therefore, the peak position and the peak value in the DSC thermogram are not absolute. According to the state of the instrument for the experiment disclosed herein, the error margin in the melting peaks is $\pm 3°$ C.

Glass transition refers to a transition of amorphous substances between elastomeric state and glassy state, which is an inherent property of the substance; the corresponding transition temperature is glass transition temperature (Tg), which is an important physical property of amorphous substances. Glass transition is a phenomenon related to the molecular motion. Therefore, glass transition temperature (Tg) mainly depends on the structure of a substance, and relatively insensitive to experimental details. According to the state of the instrument for the experiment disclosed herein, the error margin in the melting peaks is $\pm 3°$ C.

Differential scanning calorimetry (DSC) also can be used for detection and analysis whether there is crystal transformation or mixed grain phenomenon in crystalline form.

Solids having same chemical composition usually form polymorphs, or called variants, which have different crystal structures under different thermodynamic conditions, this phenomenon is called polymorphism or polyphase. When conditions of temperature and pressure change, there will be a change between variants, this phenomenon is called crystal transition. The property of crystalline forms such as mechanics, electrics, magnetics, etc, have a great change because of crystal transition. The crystal transition process could be observed in differential scanning calorimetry (DSC) thermogram when the transition temperature is within a measurable range, which is characterized by the DSC thermogram having an exothermic peak reflecting this transformation and two or more endothermic peaks which respectively are characteristic endothermic peaks of different crystalline forms before and after the transformation.

As used herein, the value of 2θ described in an X-ray powder diffraction pattern is recorded in degree)(°.

The term "substantially the same as shown in a figure" refers to an X-ray powder diffraction (XRPD) pattern or DSC pattern has at least 50%, at least 60%, at least 70%, at least 80%, at least 90%, at least 95%, or at least 99% of the peaks shown in the figure.

As used herein, when referring to a spectrum and/or to data presented in a figure, the term "peak" refers to a feature that one skilled in the art would recognize and would not be attributed to background noise.

The various novel crystalline forms of the acid addition salt referred herein are exist in a substantially pure crystalline forms.

The term "substantially pure" refers to a crystalline form that is substantially free of one or more other crystalline forms, i.e., the crystalline form has a purity of at least about 80%, at least about 85%, at least about 90%, at least about 93%, at least about 95%, at least about 98%, at least about 99%, at least about 99.5%, at least about 99.6%, at least about 99.7%, at least about 99.8%, or at least about 99.9%; or the crystalline form comprises other crystalline forms, and the percentage of the other crystalline forms in total volume or total weight is less than 20%, less than 10%, less than 5%, less than 3%, less than 1%, less than 0.5%, less than 0.1%, or less than 0.01%.

The term "substantially free" refers to the percentage of one or more other crystalline forms in total volume or total weight is less than 20%, less than 10%, less than 5%, less than 4%, less than 3%, less than 2%, less than 1%, less than 0.5%, less than 0.1%, or less than 0.01%.

As used herein, the term "relative intensity" refers to the intensity of a peak with respect to the intensity of the strongest peak in the X-ray powder diffraction pattern which is regarded as 100%.

As used in the context of the present invention, all numbers disclosed herein are approximate values, regardless of whether the word "about" is used, which means within 10%, suitably within 5% and particularly within 1% of a given value or range. Alternatively, the term "about" means within an acceptable standard error of the mean for those of ordinary skill in the art. Whenever a number having a value N is disclosed, any number having the value within N+/−1%, N+/−2%, N+/−3%, N+/−5%, N+/−7%, N+/−8% or N+/−10% is specifically disclosed, wherein "+/−" refers to plus or minus.

Unless otherwise stated, the organic acids of the invention for forming salts with compound (I) are also meant to include all isomeric (e.g., enantiomeric, diastereomeric, and geometric (conformational isomerism)) forms of the structure; for example, the R and S configurations for each asymmetric center, (Z) and (E) double bond isomers, and (Z) and (E) conformational isomers. Therefore, the salts formed from single stereochemical isomers as well as enantiomeric, diastereomeric, or geometric mixtures of the organic acid with compound (I) are within the scope disclosed herein.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereo chemistry of Organic Compounds", John Wiley&Sons, Inc., New York, 1994. The organic acid disclosed herein for forming the salt with compound (I) may contain asymmetric or chiral centers, and therefore exist in different stereoisomeric forms. It is intended that all stereoisomeric forms of the organic acid disclosed herein for forming the salt with compound (I), including, but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The term "racemic mixture" or "racemate" refers to an equimolar mixture of two enantiomeric species, devoid of optical activity.

Composition, Formulation, Administration and Uses of the Acid Addition Salts of the Compound of the Invention The characteristic of the pharmaceutical composition of the invention is the pharmaceutical composition includes a acid addition salt of compound (I) and a pharmaceutically acceptable carrier, adjuvant, or excipient. The amount of the acid addition salt of compound (I) in the composition of the invention can effectively and detectably treat, remit or prevent a disorder related to tyrosine kinase activity.

As described herein, the pharmaceutically acceptable compositions disclosed herein further comprise a pharmaceutically acceptable carrier, an adjuvant, or a vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. As the following described: Troy et al., Remington: The Science and Practice of Pharmacy, 21st ed., 2005, Lippincott Williams & Wilkins, Philadelphia, and Swarbrick et al., Encyclopedia of Pharmaceutical Technology, eds. 1988-1999, Marcel Dekker, New York, both of which are herein incorporated by reference in their entireties, discloses various carriers used in formulating pharmaceutically acceptable compositions and known techniques for the preparation thereof. Except insofar as any conventional carrier medium incompatible with the salt of compound (I) disclosed herein, such as by producing any undesirable biological effect or otherwise interacting in a deleterious manner with any other components of the pharmaceutically acceptable composition, its use is contemplated to be within the scope of this invention.

Some non-limiting examples of materials which can serve as pharmaceutically acceptable carriers include ion exchangers; aluminium; aluminum stearate; lecithin; serum proteins such as human serum albumin; buffer substances such as phosphates; glycine; sorbic acid; potassium sorbate; partial glyceride mixtures of saturated vegetable fatty acids; water; salts or electrolytes such as protamine sulfate, disodium hydrogen phosphate, potassium hydrogen phosphate, sodium chloride and zinc salts; colloidal silica; magnesium trisilicate; polyvinyl pyrrolidone; polyacrylates; waxes; polyethylene-polyoxypropylene-block polymers; wool fat; sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring, perfuming agents, preservatives and antioxidants.

The compositions disclosed herein may be administered orally, parenterally, by inhalation spray, topically, rectally, nasally, buccally, vaginally or via an implanted reservoir. It can be capsule, tablet, pellet, powder, particle and suspension in water or solution.

It can be orally administered in the following dosage forms: tablets, pellets, capsules, dispensable powders, particles or suspensions, syrup, and elixirs. Alternatively, it can be administered by external use in the form of ointment, gel, drug-containing rubberized fabric, etc. Alternatively, it can be administered parenterally in the form of sterile injectable solution or suspension.

The compositions of the invention may be administered parenterally or intraperitoneally. Solutions or suspensions of these acid addition salts of compound (I) can be prepared in water suitably mixed with a surfactant such as hydroxypropylcellulose, polyvinylpyrrolidone. Dispersions can also be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringe ability exits. It must be stable under conditions of manufacture and storage and must be preserved against the contaminating action of microorganisms such as bacterial and fungi. The carrier can be a solvent or dispersion medium containing, for example, water, ethanol (e.g., glycerol, propylene glycol and liquid polyethylene glycol), suitable mixtures thereof, and vegetable oil.

One may administer the acid addition salt of compound (I) or the pharmaceutical composition disclosed herein in a local rather than systemic manner, for example, via injection of the acid addition salt of compound (I) or the pharmaceutical composition directly into an organ in diluted formulation or sustained release formulation. Furthermore, one may administer pharmaceutical composition containing an acid addition salt of compound (I) disclosed herein in a targeted drug delivery system, for example, in a liposome coated with organ-specific antibody, the liposome will target the organ and be accepted by the organ. In addition, pharmaceutical compositions containing an acid addition salt of compound (I) disclosed herein may be provided in the form of a rapid release formulation, in the form of an extended release formulation, or in the form of an intermediate release formulation.

For administration by inhalation, the acid addition salt of compound (I) disclosed herein may be in a form as an aerosol, a mist or a powder. Pharmaceutical compositions of the acid addition salts of compound (I) disclosed herein may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges, such as, by way of example only, gelatin for use in an inhaler or insufflator may be formulated containing a powder mix of the acid addition salt of compound (I) disclosed herein and a suitable powder base such as lactose or starch.

The acid addition salts of compound (I) disclosed herein may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

The acid addition salts of compound (I) disclosed herein can be administered as the sole pharmaceutical agent or in combination with one or more other additional therapeutic (pharmaceutical) agents where the combination causes no unacceptable adverse effects. This may be of particular relevance for the treatment of hyper-proliferative diseases such as cancer. In this instance, the acid addition salt of compound (I) disclosed herein can be combined with known cytotoxic agents, single transduction inhibitors, or with other anti-cancer agents, as well as with admixtures and combinations thereof. As used herein, additional therapeutic agents that are normally administered to treat a particular disease, or condition, are known as "appropriate for the disease, or condition, being treated". As used herein, "additional therapeutic agents" includes chemotherapeutic agents and other anti-proliferative agents. For example, chemotherapeutic agents or other antiproliferative agents may be combined with the acid addition salt of compound (I) disclosed herein to treat proliferative disease or cancer.

Examples of chemotherapeutic agents or other antiproliferative agents include HDAC inhibitors including, but are not limited to, SAHA, MS-275, MGO 103, and those described in WO 2006/010264, WO 03/024448, WO 2004/069823, US 2006/0058298, US 2005/0288282, WO 00/71703, WO 01/38322, WO 01/70675, WO 03/006652, WO 2004/035525, WO 2005/030705, WO 2005/092899, and demethylating agents including, but not limited to, 5-aza-dC, Vidaza and Decitabine and those described in U.S.

Pat. Nos. 6,268,137, 5,578,716, 5,919,772, 6,054,439, 6,184,211, 6,020,318, 6,066,625, 6,506,735, 6,221,849, 6,953,783, U.S. Ser. No. 11/393,380.

In another embodiment disclosed herein, for example, chemotherapeutic agents or other anti-proliferative agents may be combined with the acid addition salt of compound (I) disclosed herein disclosed herein to treat proliferative diseases and cancer. Examples of known chemotherapeutic agents include, but are not limited to, for example, other therapies or anticancer agents that may be used in combination with the inventive anticancer agents disclosed herein and include surgery, radiotherapy (in but a few examples, gamma-radiation, neutron beam radiotherapy, electron beam radiotherapy, proton therapy, brachytherapy, and systemic radioactive isotopes, to name a few), endocrine therapy, taxanes (taxol, taxotere etc), platinum derivatives, biologic response modifiers (interferons, interleukins, and tumor necrosis factor (TNF), TRAIL receptor targeting agents and intermedium, to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, cyclophosphamide, melphalan, ifosfamide), antimetabolites (methotrexate, pemetrexed etc), purine antagonists and pyrimidine antagonists (6-mercaptopurine, 5-fluorouracil, cytarabile, gemcitabine), spindle poisons (vinblastine, vincristine, vinorelbine, paclitaxel), podophyllotoxins (etoposide, irinotecan, topotecan), antibiotics (doxorubicin, bleomycin, mitomycin), nitrosoureas (carmustine, lomustine), inorganic ions (cisplatin, carboplatin), cell cycle inhibitors (KSP mitotic kinesin inhibitors, CENP-E and CDK inhibitors), enzymes (asparaginase), and hormones (tamoxifen, leuprolide, flutamide, and megestrol), gleevec, adriamycin, dexamethasone, and cyclophosphamide. Anti-angiogenic agents (avastin and others), kinase inhibitors (imatinib, sutent, nexavar, erbitux, herceptin, tarceva, iressa and others). Agents inhibit or activat cancer pathways such as the mTOR, HIF (hypoxia induced factor) pathways and others. For a more comprehensive discussion of updated cancer therapies see, http://www.nci.nih.gov/, a list of the FDA approved oncology drugs at http://www.fda.gov/cder/cancer/druglist-rame.htm, and The Merck Manual, Eighteenth Ed. 2006, the entire contents of which are hereby incorporated by reference.

In another embodiment, the acid addition salt of compound (I) disclosed herein can be combined with cytotoxic anti-cancer agents. Examples of such agents can be found in the 13th Edition of the Merck Index (2001). These agents include, by no way of limitation, asparaginase, bleomycin, carboplatin, carmustine, chlorambucil, cisplatin, colaspase, cyclophosphamide, cytarabine, dacarbazine, dactinomycin, daunorubicin, doxorubicin (adriamycin), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, or vindesine.

Other cytotoxic drugs suitable for use with the acid addition salt of compound (I) disclosed herein include, but are not limited to, those compounds acknowledged to be used in the treatment of neoplastic diseases, such as those for example in Goodman and Gilman's The Pharmacological Basis of Therapeutics (Ninth Edition, 1996, McGraw-Hill). These agents include, by no way of limitation, aminoglutethimide, L-asparaginase, azathioprine, 5-azacytidine, cladribine, busulfan, diethylstilbestrol, 2',2'-difluorodeoxycytidine, docetaxel, erythro hydroxy nonyl adenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine or vinorelbine.

Other cytotoxic anti-cancer agents suitable for use in combination with the acid addition salt of compound (I) disclosed herein also include newly discovered cytotoxic agents, some examples of cytotoxic agents include, but are not limited to, oxaliplatin, gemcitabine, capecitabine, macrolide and its natural or synthetic derivatives, temozolomide (Quinn et al., J Clin. Oncology, 2003, 21(4), 646-651), tositumomab (BEXXAR®), trabectedin (Vidal et al., Proceedings of the American Society for Clinical Oncology, 2004, 23, abstract, 3181), and the inhibitors of the kinesin spindle protein Eg5 (Wood et al., Curr. Opin. Pharmacol. 2001, 1, 370-377).

In another embodiment, the acid addition salt of compound (I) disclosed herein can be combined with other signal transduction inhibitors. Wherein signal transduction inhibitors target the EGFR family, such as EGFR, HER-2, and HER-4 (Raymond et al., Drugs, 2000, 60 (Suppl. 1), 15-23; Harari et al., Oncogene, 2000, 19 (53), 6102-6114), and their respective ligands. Examples of such agents include, by no way of limitation, antibody therapies such as HERCEPTIN® (trastuzumab), cetuximab (erbitux), and pertuzumab. Examples of such therapies also include, by no way of limitation, small-molecule kinase inhibitors such as IRESSA® (Gefitinib), TARCEVA® (Erlotinib), TYKERB® (Lapatinib), canertinib (CI1033), AEE788 (Traxler et al., Cancer Research, 2004, 64, 4931-4941).

In another embodiment, the acid addition salt of compound (I) disclosed herein can be combined with other signal transduction inhibitors targeting receptor kinases of the split-kinase domain families (VEGFR, FGFR, PDGFR, flt-3, c-kit, c-fins, and the like), and their respective ligands. These agents include, by no way of limitation, antibodies such as bevacizumab (AVASTIN®). These agents also include, by no way of limitation, small-molecule inhibitors such as Gleevec/Imanitib, Sprycel (Dasatinib), Tasigna/Nilotinib, Nexavar (Vandetanib), Vatalanib (PTK787/ZK222584) (Wood et al., Cancer Res. 2000, 60(8), 2178-2189), Telatinib/BAY-57-9352, BMS-690514, BMS-540215, Axitinib/AG-013736, Motesanib/AMG706, Sutent/Sunitinib/SU-11248, ZD-6474 (Hennequin et al., 92nd AACR Meeting, New Orleans, Mar. 24-28, 2001, abstract 3152), KRN-951 (Taguchi et al., 95th AACR Meeting, Orlando, Fla, 2004, abstract 2575), CP-547,632 (Beebe et al., Cancer Res. 2003, 63, 7301-7309), CP-673,451 (Roberts et al., *Proceedings of the American Association of Cancer Research,* 2004, 45, abstract 3989), CHIR-258 (Lee et al., *Proceedings of the American Association of Cancer Research,* 2004, 45, abstract 2130), MLN-518 (Shen et al., Blood, 2003, 102, 11, abstract 476).

In another embodiment, the acid addition salt of compound (I) disclosed herein can be combined with inhibitors of histone deacetylase. Examples of such agents include, by no way of limitation, suberoylanilide hydroxamic acid (SAHA), LAQ-824 (Ottmann et al., *Proceedings of the American Society for Clinical Oncology,* 2004, 23, abstract 3024), LBH-589 (Beck et al., *Proceedings of the American Society for Clinical Oncology,* 2004, 23, abstract 3025), MS-275 (Ryan et al., *Proceedings of the American Associa-* tion of Cancer Research, 2004, 45, abstract 2452), FR-901228 (Piekarz et al., *Proceedings of the American Society for Clinical Oncology*, 2004, 23, abstract 3028) and MGCDOI 03 (U.S. Pat. No. 6,897,220).

In another embodiment, the acid addition salt of compound (I) disclosed herein can be combined with other anti-cancer agents such as proteasome inhibitors, and m-TOR inhibitors. These include, by no way of limitation, bortezomib (Mackay et al., *Proceedings of the American Society for Clinical Oncology*, 2004, 23, Abstract 3109), and CCI-779 (Wu et al., *Proceedings of the American Association of Cancer Research*, 2004, 45, abstract 3849). In another embodiment, the acid addition salt of compound (I) disclosed herein can be combined with other anti-cancer agents such as topoisomerase inhibitors, including but not limited to camptothecin.

Pharmaceutical compositions may be formulated in conventional manner using one or more physiologically acceptable carriers comprising facilitate processing the acid addition salt of compound (I) disclosed herein into pharmaceutical preparations. Proper formulation is dependent upon the route of administration chosen. Any of the well-known techniques, carriers, and excipients may be used as suitable and as understood in the art. Pharmaceutical compositions comprising an acid addition salt of compound (I) disclosed herein may be manufactured in a conventional manner, such as, by way of example only, by means of conventional mixing, dissolving, granulating, dragee-making, levigating, emulsifying, encapsulating, entrapping or compression processes. Pharmaceutical compositions containing an acid addition salt of compound (I) disclosed herein may be administered in therapeutically effective amounts as pharmaceutical compositions by any conventional form and route known in the art including, but not limited to: intravenous, oral, rectal, aerosol, parenteral, ophthalmic, pulmonary, transdermal, vaginal, otic, nasal, and topical administration.

The pharmaceutical compositions will include at least one pharmaceutically acceptable carrier, diluent or excipient and the acid addition salt of compound (I) disclosed herein as an active ingredient. In addition, the pharmaceutical compositions may include other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions may also contain other therapeutically valuable substances.

Methods for the preparation of compositions comprising the acid addition salt of compound (I) disclosed herein include formulating the acid addition salt of compound (I) disclosed herein with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which an acid addition salt of compound (I) disclosed herein is dissolved, emulsions comprising an acid addition salt of compound (I) disclosed herein, or a solution containing liposomes, micelles, or nanoparticles comprising an acid addition salt of compound (I) disclosed herein as disclosed herein. Semi-solid compositions include, but are not limited to, gels, suspensions and creams. The compositions may be in liquid solutions or suspensions, solid forms suitable for solution or suspension in a liquid prior to use, or as emulsions. These compositions may also contain minor amounts of nontoxic, auxiliary substances, such as wetting or emulsifying agents, pH buffering agents, and so forth.

Preferably, the acid addition salt of compound (I) disclosed herein of the invention is formulated into unit dosage forms in order to reduce the amount of drug administered and to obtain dose uniformity. The term "unit dosage form" as used herein refers to physical drug dispersion unit that patients will receive for the appropriate treatment. It will be understood, however, that the total daily usage of the acid addition salt of compound (I) disclosed herein or pharmaceutical compositions disclosed herein will be decided by the attending physician within the scope of sound medical judgment. The specific effective dose level for any particular patient or organism will depend upon a variety of factors including the disorder being treated and the severity of the disorder; the activity of the specific acid addition salt of compound (I) disclosed herein employed; the specific composition employed; the age, body weight, general health, sex and diet of the patient; the time of administration, route of administration, and rate of excretion of the specific acid addition salt of compound (I) disclosed herein employed; the duration of the treatment; drugs used in combination or coincidental with the specific compound employed, and like factors well known in the medical arts.

The effective dose of the active ingredient used can be varied with the acid addition salt of compound (I) disclosed herein used, the mode of administration and the severity degree of the disease to be treated. However, satisfactory results can be obtained, when the acid addition salt of compound (I) disclosed herein was administered with the daily dose of about 0.25-1000 mg/kg animal weight; preferably, administered with 2-4 divided doses every day, or administered in the form of sustained release. For most of the large mammals, the total daily dose is about 1-100 mg/kg, preferably about 2-80 mg/kg. Dosage forms suitable for oral administration contain about 0.25-500 mg of the active compounds intimately mixed with a solid or liquid pharmaceutically acceptable carrier. The dose can be adjusted to provide the optimal therapeutic response. In addition, according to the urgent requirements of the treatment status, several divided doses can be administered daily or the dose can be reduced proportionally.

The acid addition salt of compound (I) disclosed herein or the pharmaceutical composition can be used for preventing, managing, treating, remitting or lessening a proliferative disease in tissue or organ or atherosclerosis, pulmonary fibrosis effectively, in particular, for treating colonic carcinoma, lymphoma, colorectal cancer, small cell lung cancer, neuroblastoma, thyroid carcinoma, head and neck cancer, prostate cancer, pancreatic cancer, central nervous system cancer, malignant glioma or myeloproliferative disorders in patients.

DESCRIPTION OF THE PREFERRED EMBODIMENTS

Figure 1:
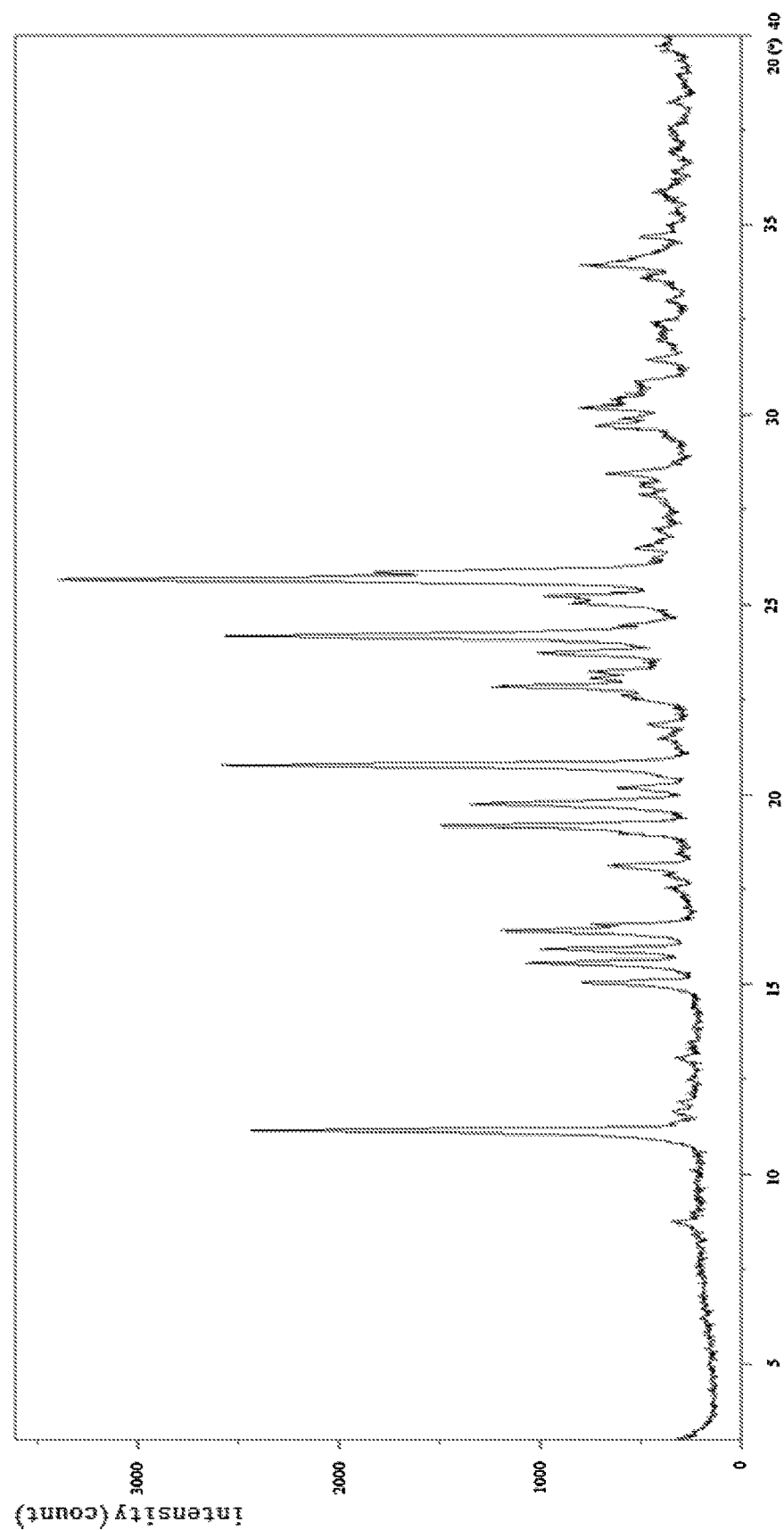
FIG. 1 provides an X-ray powder diffraction (XRPD) pattern of hydrobromide crystalline form I prepared by the method described in example 6 disclosed herein.

The invention is illustrated further by the following examples, which are not be construed as limiting the invention in scope.

In the examples described below, unless otherwise indicated all temperatures are set forth in degrees Celsius. Unless otherwise specified, the agents were purchased from Aldrich Chemical Company, Arco Chemical Company and Alfa Chemical Company, which were used directly without further purification. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd., and Qingdao Ocean Chemical Factory.

The X ray powder diffraction analysis method disclosed herein is: X-ray powder diffraction diagram was recorded on an Empyrean diffraction, using Cu-Kα radiation (45 KV, 40 mA). A thin layer was prepared from powder sample on the single-crystal silicon sample holder, and which was put on a rotary sample stage and, analyzed in the range from 3° to 40° with a 0.0167° step size. Data were collected by Data Collector software, and processed by HighScore Plus software, read by Data Viewer software.

The differential Scanning calorimetry (DSC) analysis method disclosed herein is: Differential scanning calorimetry thermogram was recorded on a TA Q2000 module with a thermoanalysis controller. The data are collected and analyzed by TA Instruments Thermal Solutions software. About 1-5 mg sample was weighed accurately in a special aluminium crucible with a lid, and heated using a linear heating device in 10° C./minute and analyzed from room temperature to about 300° C. DSC cabin was purged with dry nitrogen during use.

Sample/compound purity disclosed herein was measured by High Performance Liquid Chromatography (HPLC) using Agilent 1260 HPLC (column Model: Agilent zorbax Eclipse Plus C18) and DAD detector. Compound purity was calculated with area normalization method.

EXAMPLES

Compound I with chemical name of 1-(5-(tert-butyl) isoxazol-3-yl)-3-(4-((4-(3-morpholinopropoxy)phenyl) ethynyl)phenyl)urea was prepared by the method described in example 21 of patent application CN 105272930A (publication number). Preparation methods of an acid addition salt of compound (I) were described with reference to the following examples, the free base in the examples is 1-(5-(tert-butyl)isoxazol-3-yl)-3-(4-((4-(3-morpholinopropoxy) phenyl)ethynyl)phenyl)urea, i.e. compound (I).

Example 1 Benzene Sulfonate Crystalline Form I

1. Preparation of Benzene Sulfonate Crystalline Form I

The free base (2.05 g, 4.08 mmol) was added into ethyl acetate (87.0 mL). After the mixture was dissolved by heating to 70° C., a solution of benzenesulfonic acid (0.776 g, 4.9058 mmol) in ethyl acetate (10.0 mL) was added. The mixture was stirred at this temperature overnight. The reaction mixture was cooled to rt naturally to induce precipitation, then the mixture was filtered by suction. The filter cake was washed with ethyl acetate (5.0 mL×2) and dried in vacuo at rt to get benzene sulfonate crystalline form I (2.634 g, 97.7%).

Figure 3:
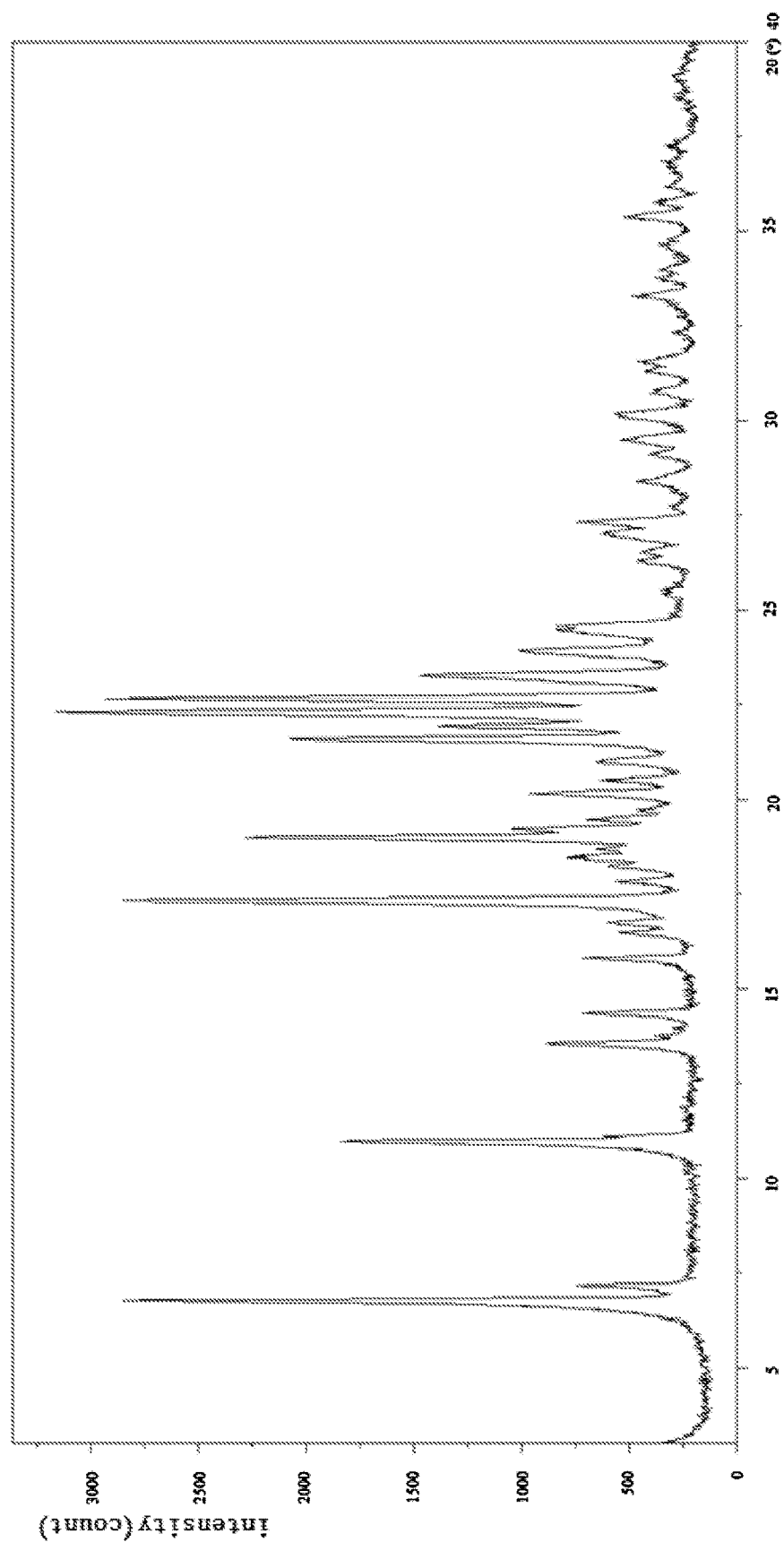
FIG. 3 provides an X-ray powder diffraction (XRPD) pattern of benzene sulfonate crystalline form I prepared by the method described in example 1 disclosed herein.

2. Identification of Benzene Sulfonate Crystalline Form I (1) The XRPD pattern was analyzed and identified by using Empyrean X-ray powder diffraction (XRPD) with Cu-Kα radiation, having the following characteristic peaks expressed in degrees 2θ at 6.74°, 7.16°, 10.95°, 13.54°, 14.33°, 15.78°, 16.46°, 16.74°, 17.30°, 17.82°, 18.20°, 18.46°, 18.69°, 18.98°, 19.21°, 19.47°, 19.72°, 20.14°, 20.49°, 20.98°, 21.56°, 21.91°, 22.27°, 22.64°, 23.23°, 23.89°, 24.45°, 24.60°, 25.46°, 26.28°, 26.53°, 26.98°, 27.30°, 27.71°, 28.38°, 29.09°, 29.47°, 30.11°, 30.74°, 31.28°, 31.54°, 33.26°, 33.85°, 34.60°, 35.36°, 35.74° and 36.69°. The error margin in 2θ of the characteristic peaks is ±0.2°. Benzene sulfonate crystalline form I prepared by the method of the example has an X-ray powder diffraction (XRPD) pattern as shown in FIG. 3.

Figure 10:
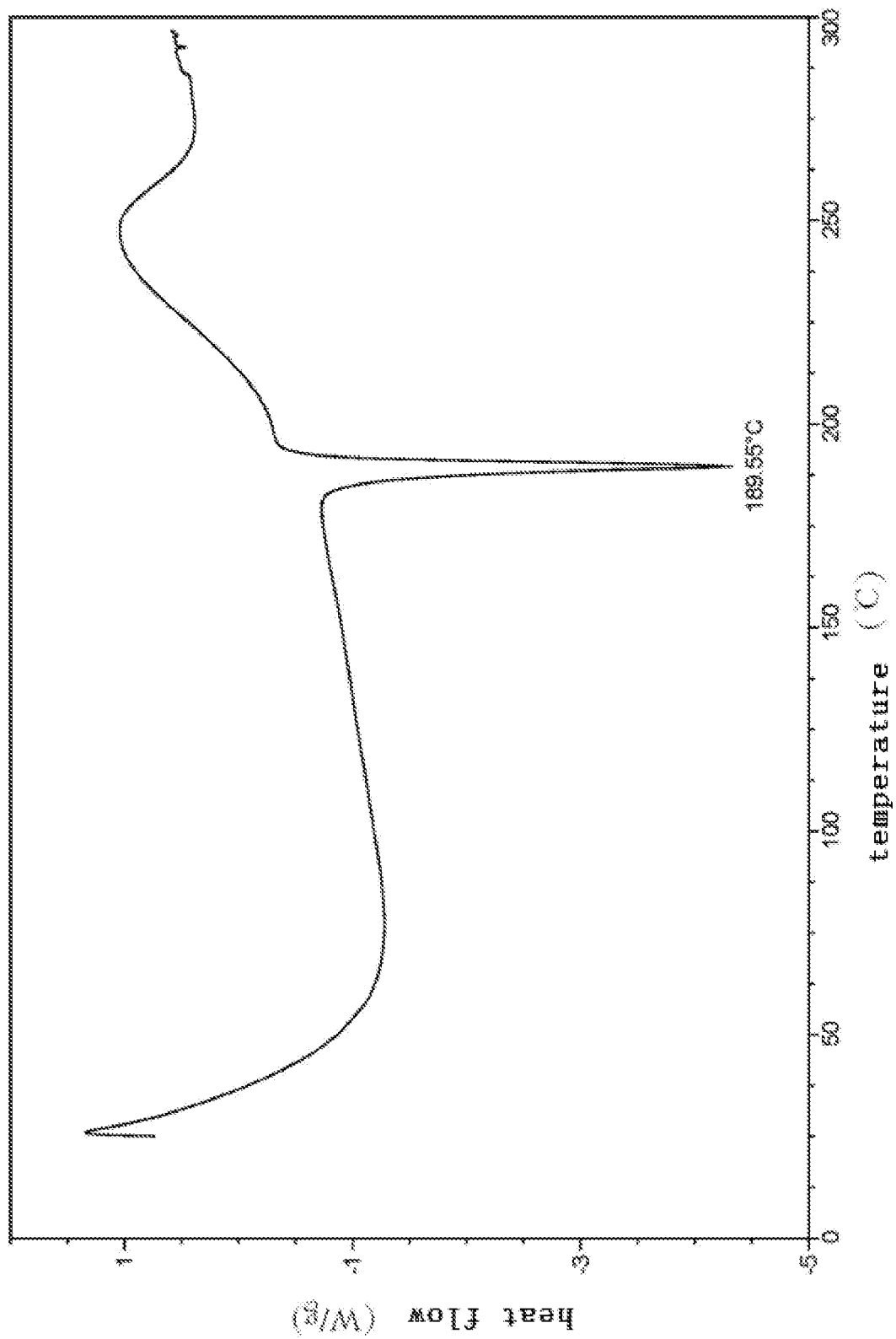
FIG. 10 provides a differential scanning calorimetry (DSC) thermogram of benzene sulfonate crystalline form I prepared by the method described in example 1 disclosed herein.

(2) The DSC thermogram was analyzed and identified by using TA Q2000 differential scanning calorimetry (DSC) with a scan rate of 10° C./minute, comprising an endothermic peak at 189.55° C. The error margin of the endothermic peaks is ±3° C. Benzene sulfonate crystalline form I prepared by the method of the example has a differential scanning calorimetry (DSC) thermogram as shown in FIG. 10.

Example 2 Benzene Sulfonate Crystalline Form II

1. Preparation of Benzene Sulfonate Crystalline Form II

The free base (103 mg, 0.205 mmol) was dissolved in 1,4-dioxane (4.0 mL), and a solution of benzenesulfonic acid (39.4 mg, 0.249 mmol) in 1,4-dioxane (0.5 mL) was added. The mixture was stirred at room temperature for 4 hours and filtered by suction. The filter cake was dried in vacuo at room temperature to get benzene sulfonate crystalline form II (133 mg, 98.02%).

Figure 4:
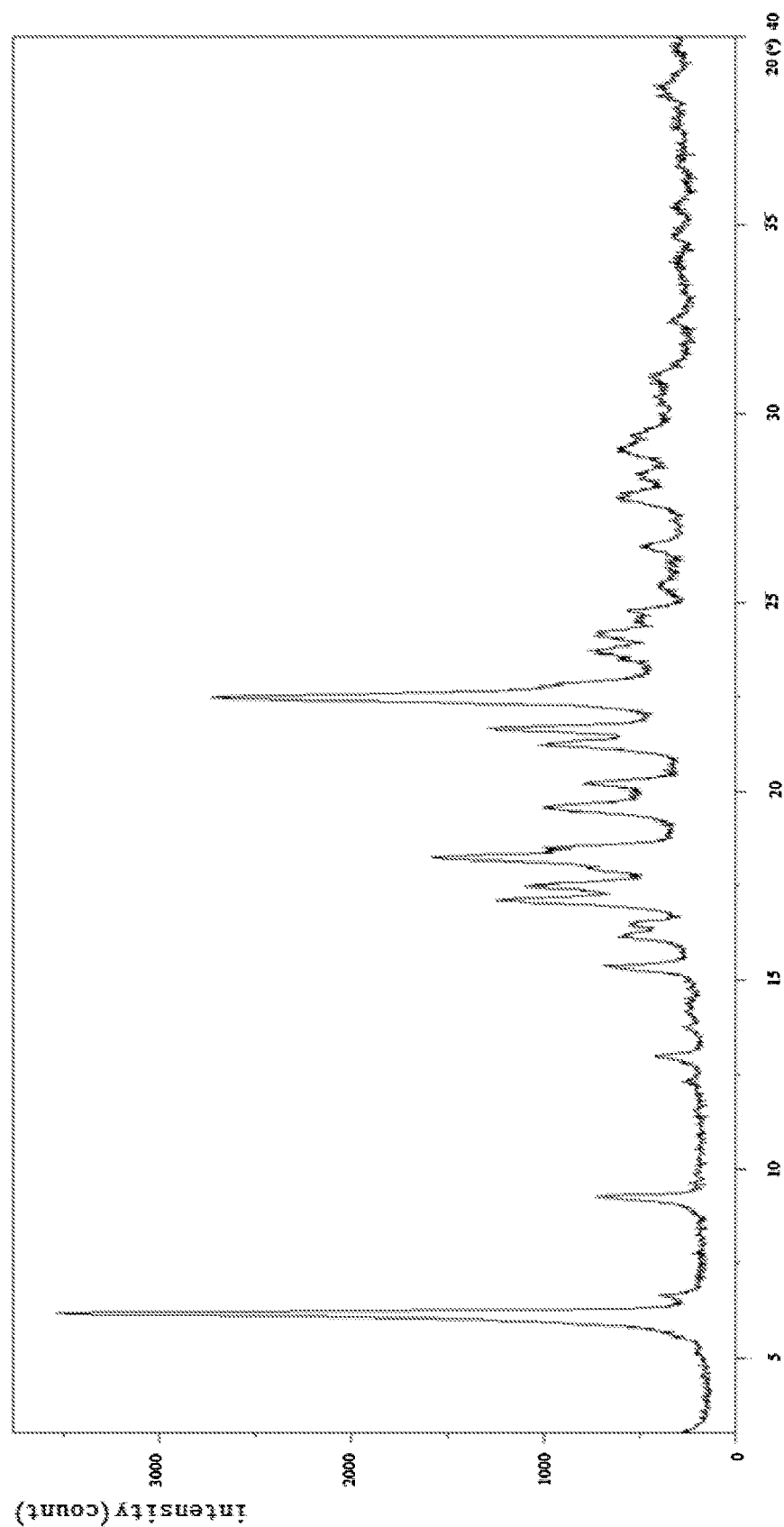
FIG. 4 provides an X-ray powder diffraction (XRPD) pattern of benzene sulfonate crystalline form II prepared by the method described in example 2 disclosed herein.

2. Identification of Benzene Sulfonate Crystalline Form II (1) The XRPD pattern was analyzed and identified by using Empyrean X-ray powder diffraction (XRPD) with Cu-Kα radiation, which has the following characteristic peaks expressed in degrees 2θ at 6.14°, 6.66°, 9.22°, 12.31°, 12.97°, 15.33°, 16.17°, 16.48°, 17.10°, 17.49°, 18.23°, 18.53°, 19.57°, 20.18°, 21.23°, 21.63°, 22.49°, 23.69°, 24.18°, 24.66°, 25.52°, 26.46°, 27.78°, 28.34°, 29.15°, 30.64°, 30.99°, 32.45°, 33.93°, 34.70°, 35.48° and 38.57°. The error margin in 2θ of the characteristic peaks is ±0.2°. Benzene sulfonate crystalline form II prepared by the method of the example has an X-ray powder diffraction (XRPD) pattern as shown in FIG. 4.

Figure 11:
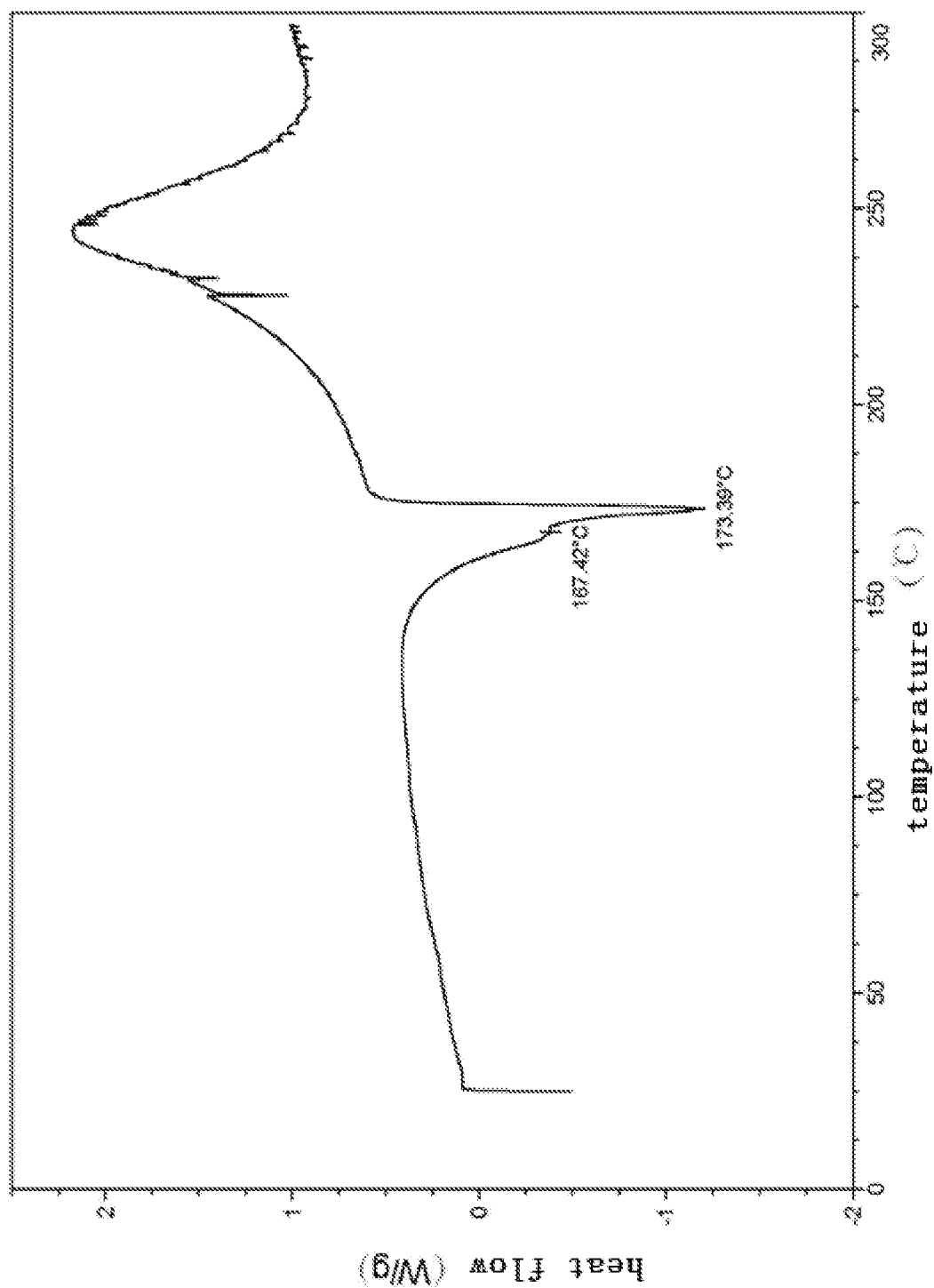
FIG. 11 provides a differential scanning calorimetry (DSC) thermogram of benzene sulfonate crystalline form II prepared by the method described in example 2 disclosed herein.

(2) The DSC thermogram was analyzed and identified by using TA Q2000 differential scanning calorimetry (DSC) with a scan rate of 10° C./minute, comprising endothermic peaks at 167.42° C. and 173.39° C. The error margin of the endothermic peaks is ±3° C. Benzene sulfonate crystalline form II prepared by the method of the example has a differential scanning calorimetry (DSC) thermogram as shown in FIG. 11.

Example 3 Benzene Sulfonate Crystalline Form III

1. Preparation of Benzene Sulfonate Crystalline Form III

The free base (73.9 mg, 0.147 mmol) was dissolved in dichloromethane (2.0 mL). After the solid was dissolved completely, benzenesulfonic acid (30.2 mg, 0.191 mmol) was added. The mixture was stirred at room temperature for 5 hours and filter by suction. The filter cake was washed with DCM (2.0 mL) and dried at 120° C. in vacuo overnight to get benzene sulfonate crystalline form III (88.4 mg, 91.0%).

Figure 5:
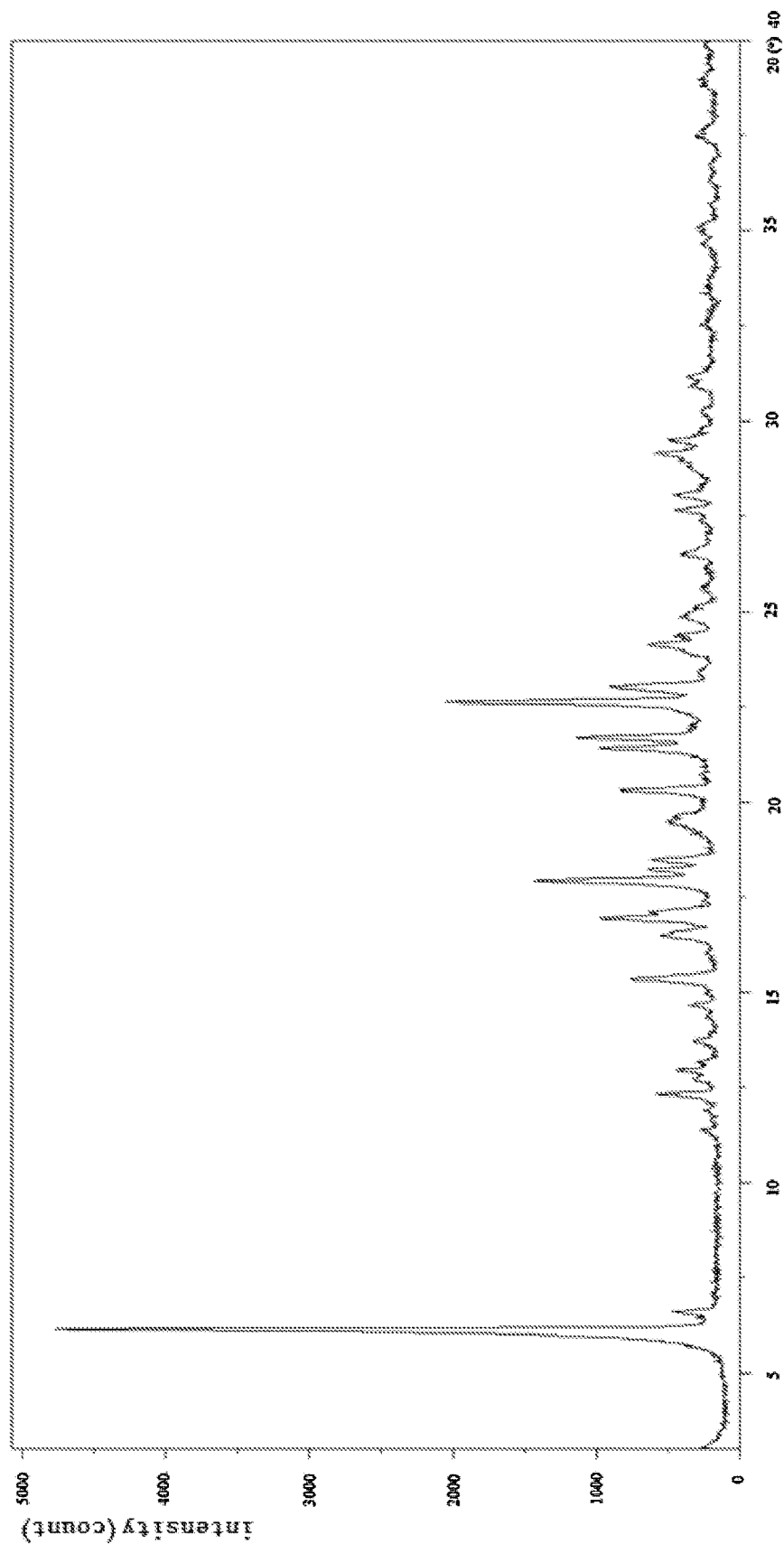
FIG. 5 provides an X-ray powder diffraction (XRPD) pattern of benzene sulfonate crystalline form III prepared by the method described in example 3 disclosed herein.

2. Identification of Benzene Sulfonate Crystalline Form III (1) The XRPD pattern was analyzed and identified by using Empyrean X-ray powder diffraction (XRPD) with Cu-Kα radiation, having the following characteristic peaks expressed in degrees 2θ at 6.12°, 6.61°, 11.36°, 11.89°, 12.31°, 12.72°, 12.95°, 13.17°, 13.71°, 14.64°, 15.33°, 16.49°, 16.93°, 17.11°, 17.92°, 18.21°, 18.46°, 19.49°, 20.29°, 21.38°, 21.67°, 22.60°, 22.99°, 24.10°, 24.37°, 24.89°, 25.61°, 26.52°, 27.63°, 28.03°, 29.07°, 29.49°, 30.22°, 30.92°, 31.16°, 32.55°, 33.53°, 34.96°, 37.51° and 38.94°. The error margin in 2θ of the characteristic peaks is ±0.2°. Benzene sulfonate crystalline form III prepared by the method of the example has an X-ray powder diffraction (XRPD) pattern as shown in FIG. 5.

Figure 12:
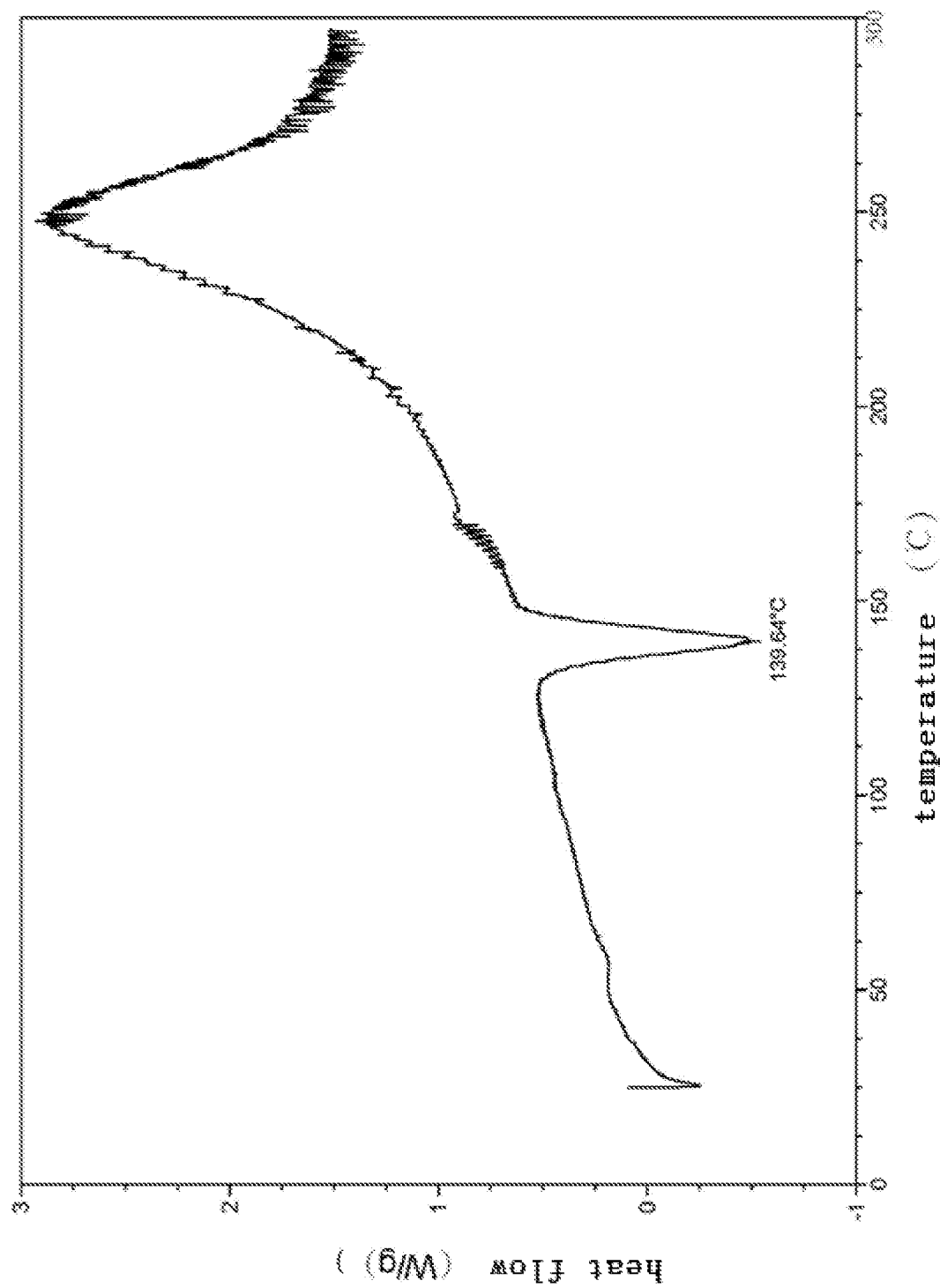
FIG. 12 provides a differential scanning calorimetry (DSC) thermogram of benzene sulfonate crystalline form III prepared by the method described in example 3 disclosed herein.

(2) The DSC thermogram was analyzed and identified by using TA Q2000 differential scanning calorimetry (DSC) with a scan rate of 10° C./minute, comprising an endothermic peak at 139.64° C. The error margin of the endothermic peaks is ±3° C. Benzene sulfonate crystalline form III prepared by the method of the example has a differential scanning calorimetry (DSC) thermogram as shown in FIG. 12.

Example 4 Benzene Sulfonate Crystalline Form IV

1. Preparation of Benzene Sulfonate Crystalline Form IV

The above benzene sulfonate crystalline form II (1.16 g, 1.76 mmol) was added into acetone (50.0 mL). The mixture was triturated and refluxed for 3 days, and cooled to room temperature naturally, and then filtered. The filter cake was washed with a little acetone and dried at 60° C. in vacuo to get benzene sulfonate crystalline form IV (0.89 g, 77%).

Figure 6:
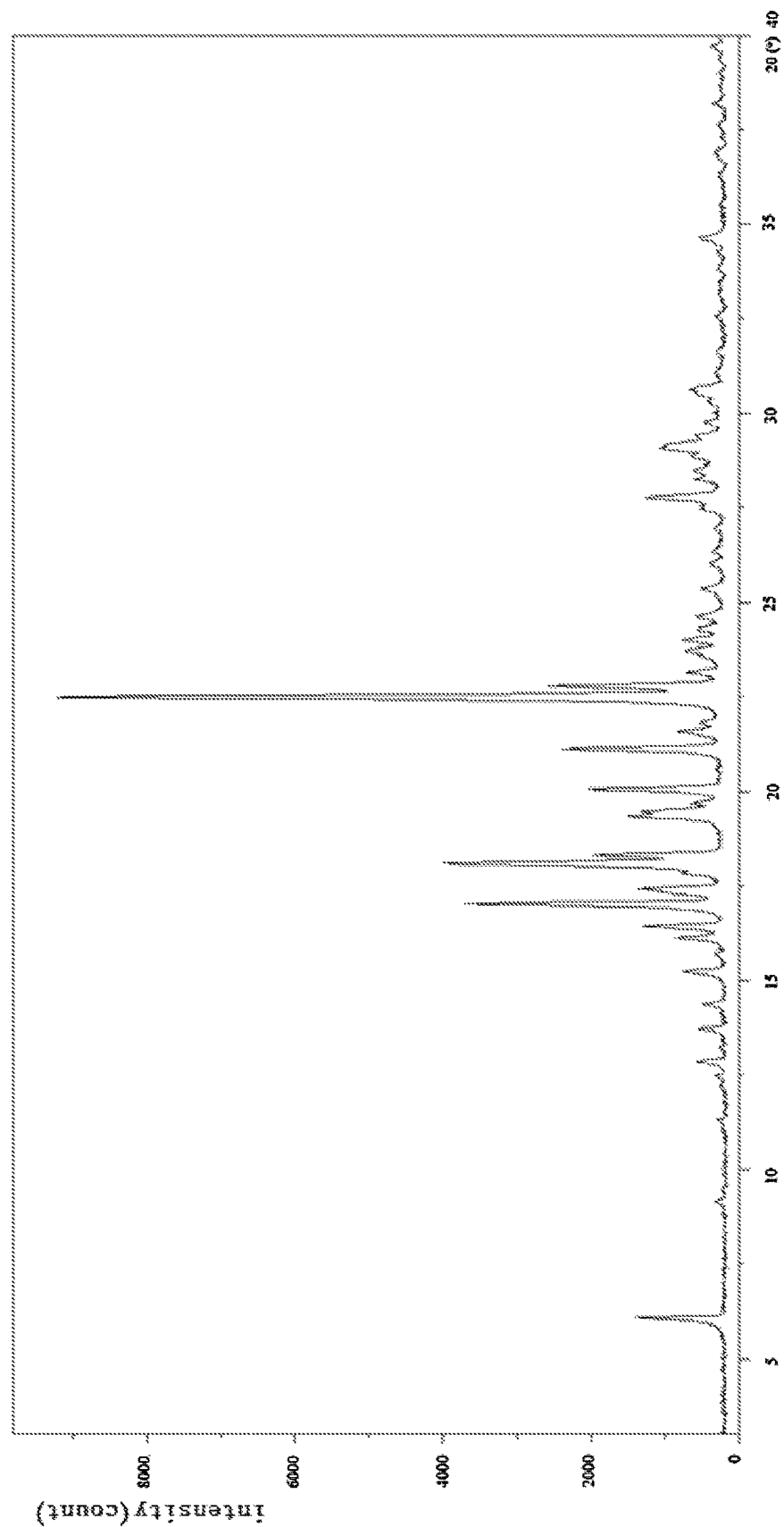
FIG. 6 provides an X-ray powder diffraction (XRPD) pattern of benzene sulfonate crystalline form IV prepared by the method described in example 4 disclosed herein.

2. Identification of Benzene Sulfonate Crystalline Form IV (1) The XRPD pattern was analyzed and identified by using Empyrean X-ray powder diffraction (XRPD) with Cu-Kα radiation, having the following characteristic peaks expressed in degrees 2θ at 6.07°, 9.15°, 11.28°, 12.22°, 12.47°, 12.85°, 13.71°, 14.36°, 15.21°, 15.67°, 16.11°, 16.42°, 17.01°, 17.38°, 17.84°, 18.08°, 18.31°, 19.34°, 19.47°, 19.69°, 20.05°, 21.10°, 21.56°, 21.80°, 22.47°, 22.77°, 23.14°, 23.68°, 24.01°, 24.29°, 24.62°, 25.34°, 26.01°, 26.36°, 26.96°, 27.48°, 27.75°, 28.23°, 28.45°, 29.06°, 29.18°, 29.40°, 29.74°, 30.48°, 30.64°, 31.07°, 31.61°, 32.56°, 33.16° and 33.44°. The error margin in 2θ of the characteristic peaks is ±0.2°. Benzene sulfonate crystalline form IV prepared by the method of the example has an X-ray powder diffraction (XRPD) pattern as shown in FIG. 6.

Figure 13:
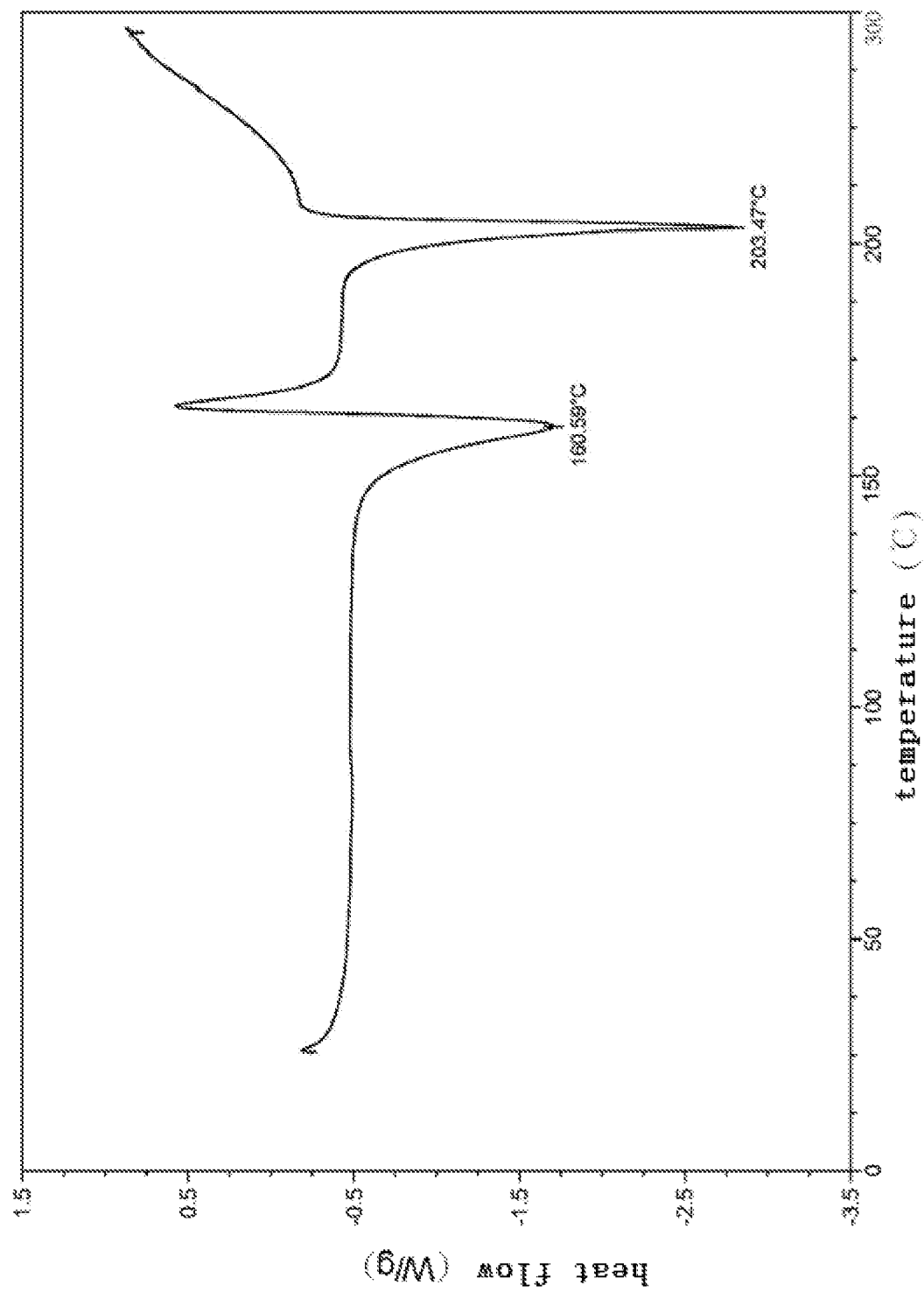
FIG. 13 provides a differential scanning calorimetry (DSC) thermogram of benzene sulfonate crystalline form IV prepared by the method described in example 4 disclosed herein.

(2) The DSC thermogram was analyzed and identified by using TA Q2000 differential scanning calorimetry (DSC) with a scan rate of 10° C./minute, comprising endothermic peaks at 160.59° C. and 203.47° C. The error margin of the endothermic peaks is ±3° C. Benzene sulfonate crystalline form IV prepared by the method of the example has a differential scanning calorimetry (DSC) thermogram as shown in FIG. 13.

Example 5 Benzene Sulfonate Crystalline Form V

1. Preparation of Benzene Sulfonate Crystalline Form V

The above benzene sulfonate crystalline form IV (807 mg, 1.22 mmol) was heated to 179° C. and maintained at this temperature for 3 min, and then cooled to room temperature naturally to get benzene sulfonate crystalline form V (780 mg, 97%).

Figure 7:
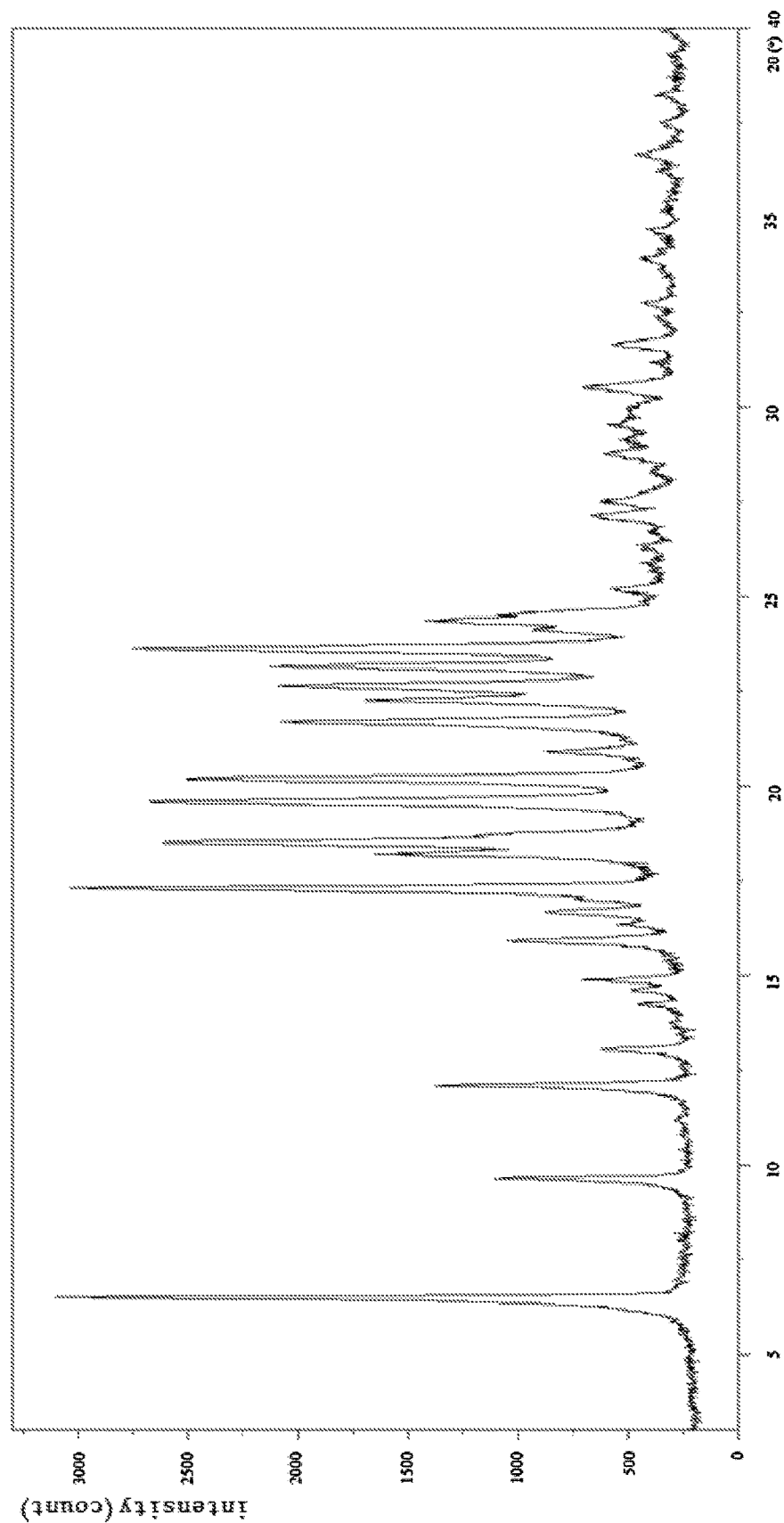
FIG. 7 provides an X-ray powder diffraction (XRPD) pattern of benzene sulfonate crystalline form V prepared by the method described in example 5 disclosed herein.

2. Identification of Benzene Sulfonate Crystalline Form V (1) The XRPD pattern was analyzed and identified by using Empyrean X-ray powder diffraction (XRPD) with Cu-Kα radiation, having the following characteristic peaks expressed in degrees 2θ at 6.49°, 9.62°, 12.08°, 13.04°, 14.22°, 14.60°, 14.87°, 15.90°, 16.33°, 16.66°, 17.28°, 18.18°, 18.50°, 19.57°, 20.16°, 20.89°, 21.66°, 22.24°, 22.60°, 23.13°, 23.60°, 24.09°, 24.33°, 24.55°, 25.17°, 26.17°, 27.08°, 27.50°, 28.73°, 29.09°, 29.62°, 30.50°, 31.62°, 32.71°, 33.87°, 34.62°, 36.64°, 37.46°, 38.22° and 39.94°. The error margin in 2θ of the characteristic peaks is ±0.2°. Benzene sulfonate crystalline form V prepared by the method of the example has an X-ray powder diffraction (XRPD) pattern as shown in FIG. 7.

Figure 14:
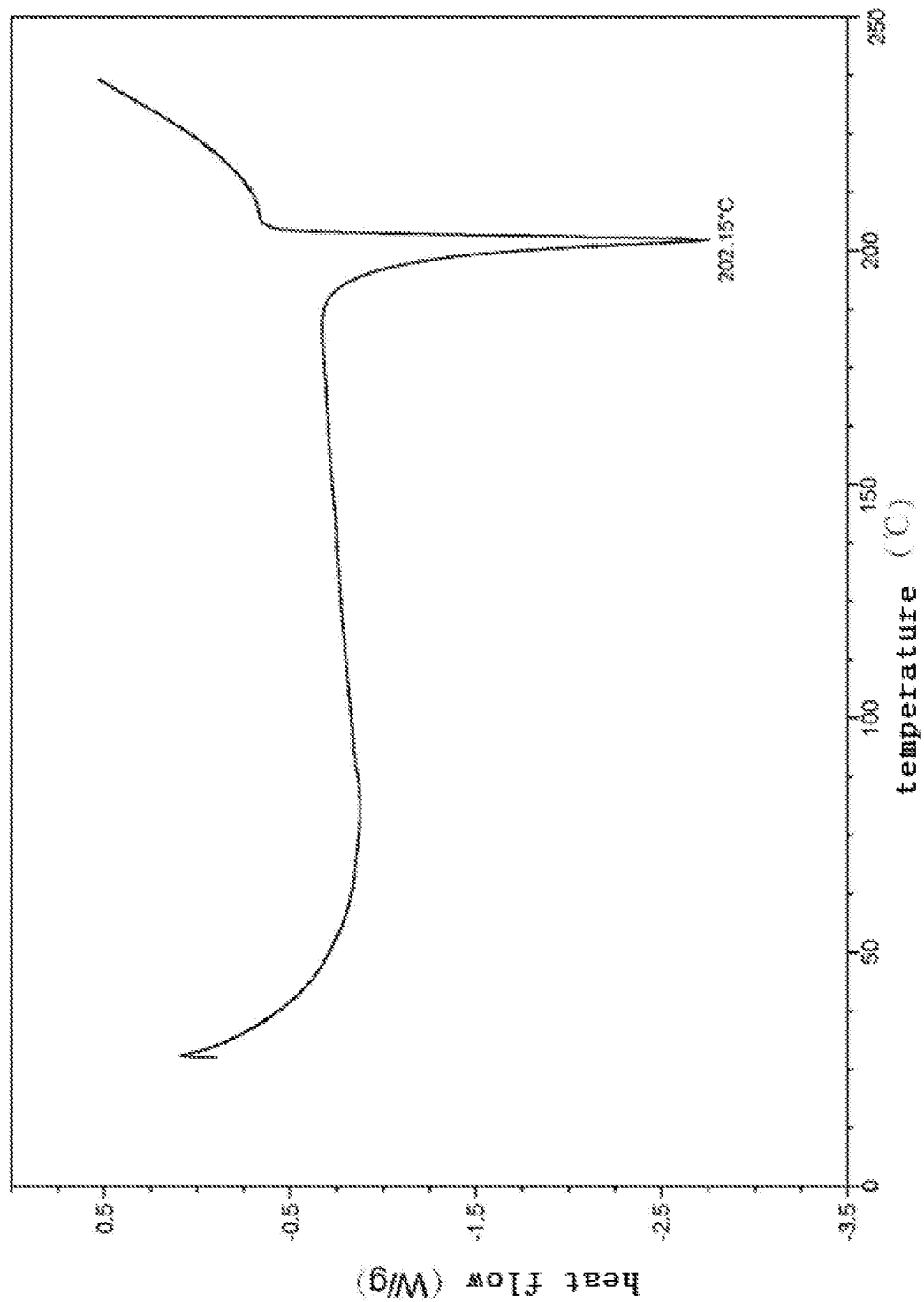
FIG. 14 provides a differential scanning calorimetry (DSC) thermogram of benzene sulfonate crystalline form V prepared by the method described in example 5 disclosed herein.

(2) The DSC thermogram was analyzed and identified by using TA Q2000 differential scanning calorimetry (DSC) with a scan rate of 10° C./minute, comprising an endothermic peak at 202.15° C. The error margin of the endothermic peaks is ±3° C. Benzene sulfonate crystalline form V prepared by the method of the example has a differential scanning calorimetry (DSC) thermogram as shown in FIG. 14.

Example 6 Hydrobromide Crystalline Form I

1. Preparation of Hydrobromide Crystalline Form I

The free base (1.72 g, 3.42 mmol) was added to ethanol (250.0 mL), the resulting mixture was dissolved by heating and refluxing, and then a mixture of hydrobromic acid (0.745 g, 0.5 mL, 4.42 mmol) and ethanol (5.0 mL) was added. Solid precipitated out, and the mixture was stirred at this temperature overnight. The mixture was cooled to room temperature naturally and filtered by suction. The filter cake was washed with ethanol (5.0 mL×2) and dried in vacuo at room temperature to get hydrobromide crystalline form I (1.732 g, 86.7%).

2. Identification of Hydrobromide Crystalline Form I (1) The XRPD pattern was analyzed and identified by using Empyrean X-ray powder diffraction (XRPD) with Cu-Kα radiation, having the following characteristic peaks expressed in degrees 2θ at 8.28°, 11.13°, 11.65°, 11.88°, 13.05°, 15.02°, 15.54°, 15.90°, 16.40°, 16.57°, 17.50°, 18.09°, 19.15°, 19.74°, 20.16°, 20.74°, 21.47°, 21.81°, 22.56°, 22.83°, 23.03°, 23.20°, 23.70°, 24.16°, 24.47°, 25.03°, 25.21°, 25.65°, 25.85°, 26.50°, 27.96°, 28.43°, 29.70°, 30.26°, 30.79°, 31.44°, 32.16°, 33.57°, 33.96°, 34.68°, 35.83°, 36.89°, 37.42° and 38.23°. The error margin in 2θ of the characteristic peaks is ±0.2°. Hydrobromide crystalline form I prepared by the method of the example has an X-ray powder diffraction (XRPD) pattern as shown in FIG. 1.

Figure 8:
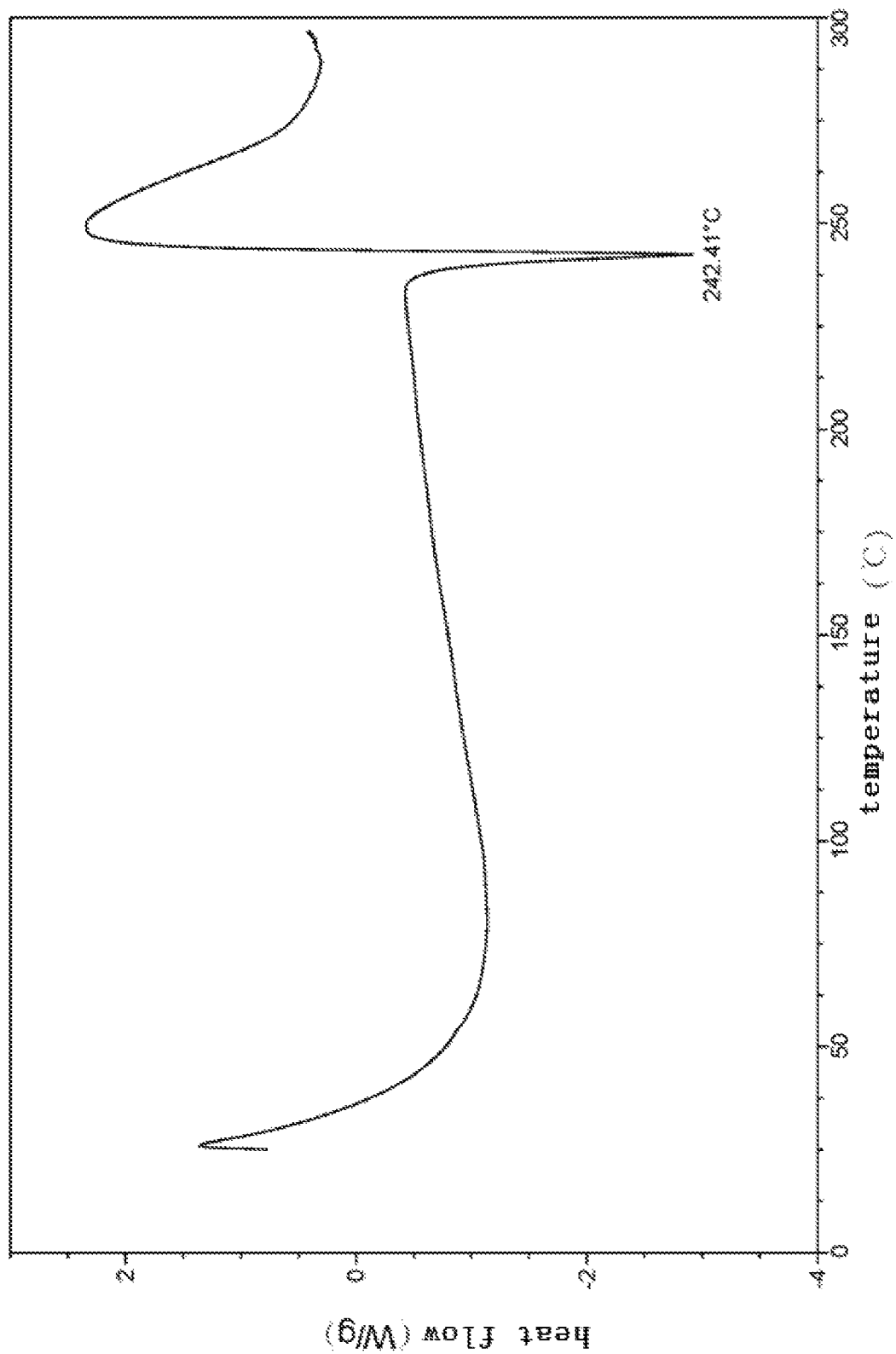
FIG. 8 provides a differential scanning calorimetry (DSC) thermogram of hydrobromide crystalline form I prepared by the method described in example 6 disclosed herein.

(2) The DSC thermogram was analyzed and identified by using TA Q2000 differential scanning calorimetry (DSC) with a scan rate of 10° C./minute, comprising an endothermic peak at 242.41° C. The error margin of the endothermic peaks is ±3° C. Hydrobromide crystalline form I prepared by the method of the example has a differential scanning calorimetry (DSC) thermogram as shown in FIG. 8.

Example 7 Hydrochloride Crystalline Form I

1. Preparation of Hydrochloride Crystalline Form I

The free base (2.0 g, 4.0 mmol) was dissolved in acetone (193.0 mL) at room temperature, and then a self-made solution of HCl in ethyl acetate (1.5 mL, 4.7 mmol) and acetone (7.0 mL) was added dropwise slowly. Solid precipitated out, and the mixture was stirred overnight. The mixture was filtered by suction. The filter cake was washed with acetone (5.0 mL×2) and dried in vacuo at room temperature to get hydrochloride crystalline form I (2.04 g, 95%).

Figure 2:
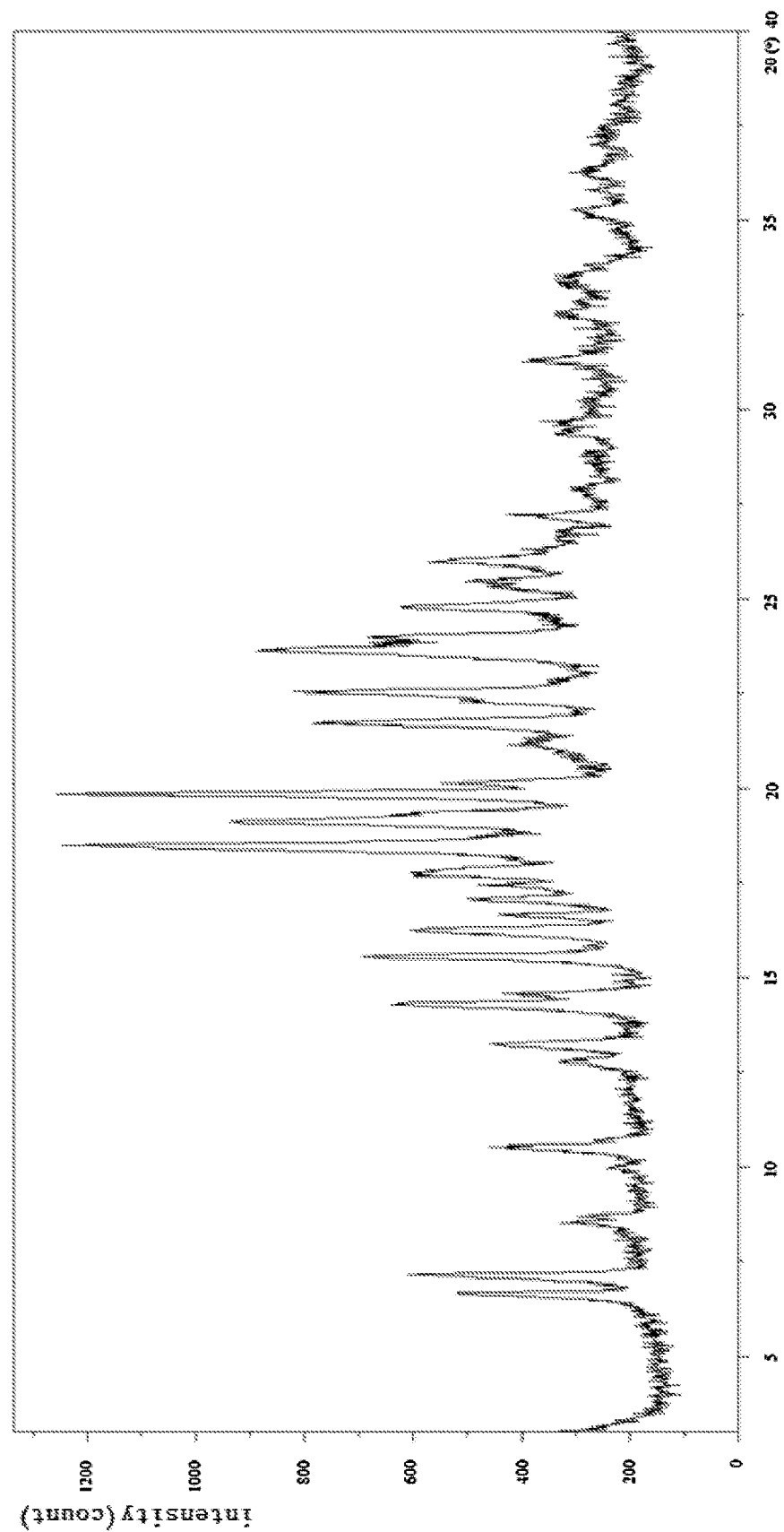
FIG. 2 provides an X-ray powder diffraction (XRPD) pattern of hydrochloride crystalline form I prepared by the method described in example 7 disclosed herein.

2. Identification of Hydrochloride Crystalline Form I (1) The XRPD pattern was analyzed and identified by using Empyrean X-ray powder diffraction (XRPD) with Cu-Kα radiation, which has the following characteristic peaks expressed in degrees 2θ at 6.63°, 7.11°, 8.53°, 10.50°, 12.76°, 13.22°, 14.26°, 14.54°, 15.53°, 16.21°, 16.63°, 17.05°, 17.41°, 17.77°, 18.45°, 19.14°, 19.83°, 20.13°, 21.15°, 21.70°, 22.48°, 23.62°, 23.97°, 24.77°, 25.37°, 26.01°, 27.15°, 27.84°, 29.57°, 31.29°, 32.54°, 33.38°, 35.19° and 36.27°. The error margin in 2θ of the characteristic peaks is ±0.2°. Hydrochloride crystalline form I prepared by the method of the example has an X-ray powder diffraction (XRPD) pattern as shown in FIG. 2.

Figure 9:
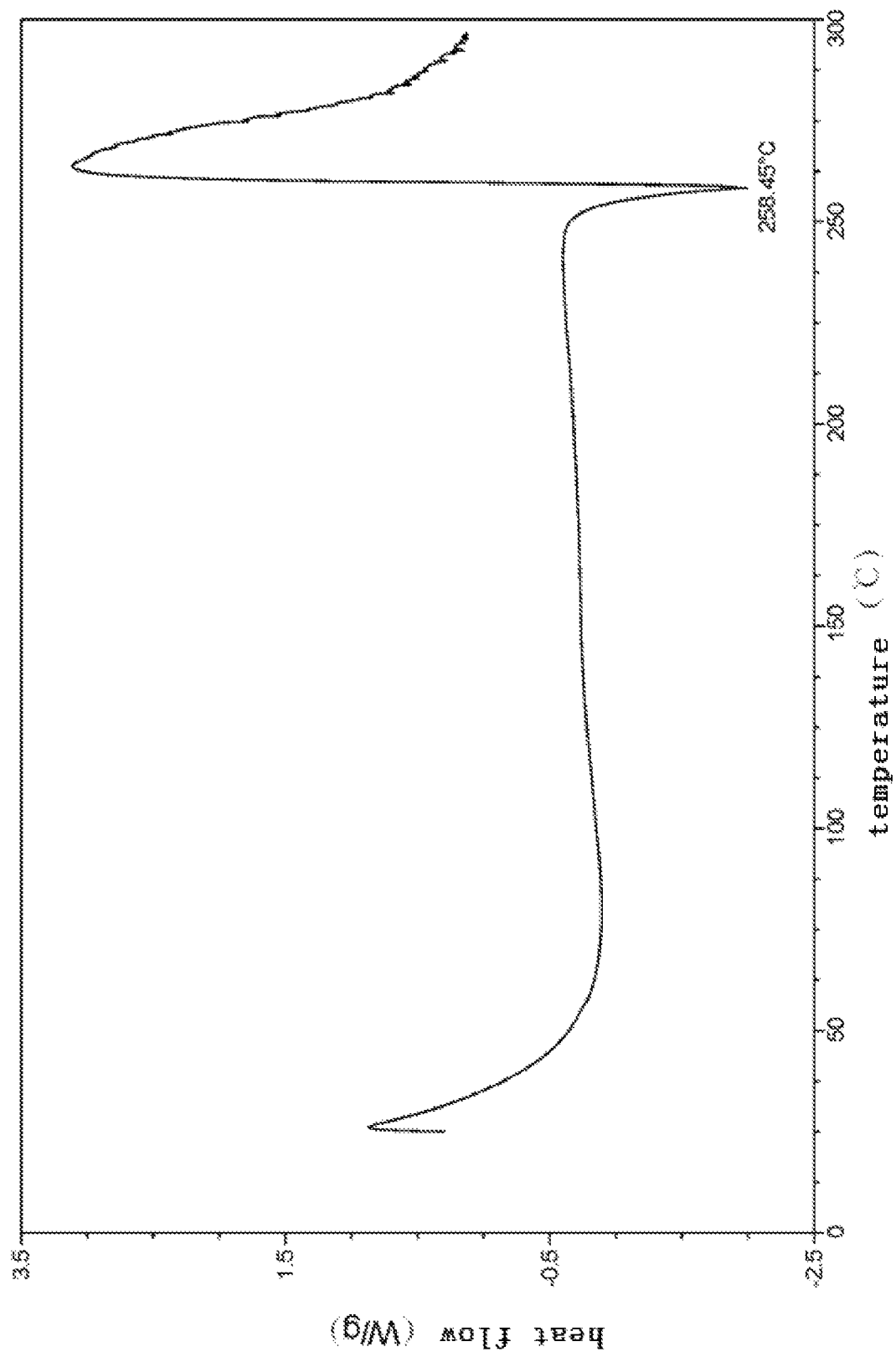
FIG. 9 provides a differential scanning calorimetry (DSC) thermogram of hydrochloride crystalline form I prepared by the method described in example 7 disclosed herein.

(2) The DSC thermogram was analyzed and identified by using TA Q2000 differential scanning calorimetry (DSC) with a scan rate of 10° C./minute, comprising an endothermic peak at 258.45° C. The error margin of the endothermic peaks is ±3° C. Hydrochloride crystalline form I prepared by the method of the example has a differential scanning calorimetry (DSC) thermogram as shown in FIG. 9.

Example 8 Pharmacokinetics Experiments of the Salts of Compound (I) Disclosed Herein The free base 1-(5-(tert-butyl)isoxazol-3-yl)-3-(4-((4-(3-morpholinopropoxy)phenyl) ethynyl)phenyl)urea, various salts or crystalline forms thereof were filled into capsules for oral administration respectively. Male Beagle dogs (6-10 kg) were grouped randomly, each group has 3, one was administered with free base by oral, others with various salts or crystalline forms thereof by oral at a dosage of 5 mg/kg. Blood samples were collected at 0.25, 0.5, 1.0, 2.0, 4.0, 6.0, 8.0, 12 and 24 hours after the administration. Standard curve was plotted based on concentrations of the samples in a suitable range, the concentrations of test compounds in plasma samples were determined by using Agilent 6430 LC-MS/MS under MRM mode, and quantitative analysis was performed. Pharmacokinetic parameters were calculated according to drug concentration-time curve using a noncompartmental method by WinNonLin 6.3 software. The results were shown as table 1.

TABLE 1

Pharmacokinetics experiments of the salts of compound (I) disclosed herein

| Group | Tmax (h) | Cmax (ng/ml) | $AUC_{last}$ (h*ng/ml) | $AUC_{INF}$ (h*ng/ml) | $T_{1/2}$ (h) | $MRT_{INF}$ (h) |
|---|---|---|---|---|---|---|
| Free base | 1.67 | 60.9 | 389 | 423 | 5.95 | 7.52 |
| Benzene sulfonate crystaline form I | 1 | 92.3 | 575 | 592 | 5.26 | 6.55 |
| Hydrobromide crystaline form I | 1.33 | 36.4 | 401 | 225 | 6.64 | 8.54 |
| Hydrochloride crystaline form I | 1.67 | 51.2 | 358 | 371 | 4.86 | 6.5 |

Conclusion:

It can be known from table 1 that the salts of compound (I) disclosed herein have higher exposure level compared with the free base 1-(5-(tert-butyl)isoxazol-3-yl)-3-(4-((4-(3-morpholinopropoxy)phenyl)ethynyl)phenyl)urea in beagle dogs. Wherein, example 1 (benzene sulfonate crystalline form I) has a higher exposure level and a faster absorption.

Example 9 Stability Experiments of Benzene Sulfonate Crystalline Form I Disclosed Herein High temperature test: an appropriate amount of sample was put in a flat weighing bottle in the form of a thin layer of ≤5 mm, under a temperature of 60° C.±2° C. for 10 days. Samples were taken at fifth and tenth day, appearance was observed and purity was detected by HPLC. The results were shown as table 2.

High Humidity Test:

an appropriate amount of sample was put in a flat weighing bottle in the form of a thin layer of ≤5 mm, under a temperature of 25° C. and RH 90%±5% for 10 days. Samples were taken at fifth and tenth day, appearance was observed and purity was detected by HPLC. The results were shown as table 2.

Light Test:

an appropriate amount of sample was put in a flat weighing bottle in the form of a thin layer of ≤5 mm, and the sample in the flat weighting bottle without sealing was placed in light box (with UV) under the condition of illumination of 4500±500 lx, UV≥0.7 w/m² for 13 days. Purity of the samples was detected respectively at the 5th and 13th day by sampling. The results were shown as table 2.

TABLE 2

| | Conditions | | | | | | | | |
|---|---|---|---|---|---|---|---|---|---|
| | High temperature (60° C. ± 2° C.) | | | High humidity (25° C., RH 90% ± 5%) | | | illumination | | |
| Time | 0 day | 5 days | 10 days | 0 day | 5 days | 10 days | 0 day | 5 days | 13 days |
| Appearance | yellow solid | yellow solid | yellow solid | yellow solid | yellow solid | yellow solid | yellow solid | yellow solid | yellow solid |
| Hygroscopic weight gain/% | N/A | N/A | N/A | N/A | 0.388 | 1.100 | N/A | N/A | N/A |
| Purity/% | 98.61 | 98.64 | 98.61 | 98.61 | 98.59 | 98.59 | 98.61 | 98.67 | 98.71 |

Stability experiments of benzene sulfonate crystaline form I disclosed herein

Conclusion:

It can be known from table 2 that the appearance and purity of benzene sulfonate crystalline form I disclosed herein have not been changed distinctly under the condition of high temperature (60° C.±2° C.), high humidity (25° C., RH 90%±5%) and illumination, and hygroscopic weight gain is 1.100% under high humidity for 10 days, benzene sulfonate crystalline form I has slightly hygroscopicity. In conclusion, benzene sulfonate crystalline form I disclosed herein has a better stability under various conditions and is suitable for pharmacy use.

Example 10 Hygroscopicity Experiments of the Salts of the Invention

An appropriate amount of sample was took, hygroscopicity of which was detected on dynamic moisture absorption instrument. The results proved that the salts provided herein are not easy to be influenced by high humidity to deliquesce.

The above contents are merely basic descriptions under the idea of the present invention, any equivalent modifications based on the technical schemes of the invention are all within the claimed scope of the invention.

Reference throughout this specification to "an embodiment," "some embodiments," "one embodiment", "another example," "an example," "a specific examples," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific examples," or "in some examples," in various places throughout this specification are not necessarily referring to the same embodiment or example of the present disclosure. Furthermore, the particular features, structures, materials, or characteristics may be combined in any suitable manner in one or more embodiments or examples. In addition, those skilled in the art can integrate and combine different embodiments or examples of the specification or the features of them as long as they are not contradictory to one another.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A pharmaceutically acceptable acid addition salt of compound (I),

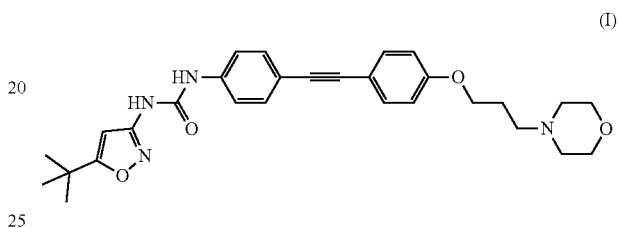

(I)

wherein the acid addition salt is:

benzene sulfonate crystalline I that has an X-ray powder diffraction pattern comprising one or more peaks expressed as 2θ at 6.74°±0.2°, 17.30°±0.2°, 18.98°±0.2°, 22.27°±0.2°, and 22.64°±0.2°; or benzene sulfonate crystalline II that has an X-ray powder diffraction pattern comprising one or more peaks expressed as 2θ at 6.14°±0.2°, 17.10°±0.2°, 18.23°±0.2°, 21.63°±0.2°, and 22.49°±0.2°; or benzene sulfonate crystalline III that has an X-ray powder diffraction pattern comprising one or more peaks expressed as 2θ at 6.12°±0.2°, 16.93°+0.2°, 17.92°+0.2°, 21.67°±0.2°, and 22.60°±0.2°; or benzene sulfonate crystalline IV that has an X-ray powder diffraction pattern comprising one or more peaks expressed as 2θ at 17.01°±0.2°, 18.08°±0.2°, 21.10°±0.2°, 22.47°±0.2°, and 22.77°±0.2°; or benzene sulfonate crystalline V that has an X-ray powder diffraction pattern comprising one or more peaks expressed as 2θ at 6.49°±0.2°, 17.28°±0.2°, 18.50°±0.2°, 19.57°±0.2°, and 23.60°±0.2°.

2. The acid addition salt of claim 1, wherein the salt is the benzene sulfonate crystalline I and the X-ray powder diffraction pattern further comprises one or more peaks expressed as 2θ at 10.95°±0.2°, 21.56°±0.2°, 21.91°±0.2°, 23.23°±0.2°, and 23.89°±0.2°.

3. The acid addition salt of claim 1, wherein the salt is the benzene sulfonate crystalline I and the X-ray powder diffraction pattern further comprises one or more peaks expressed as 2θ at 7.16°±0.2°, 10.95°±0.2°, 13.54°±0.2°, 14.33°±0.2°, 15.78°±0.2°, 16.46°±0.2°, 16.74°±0.2°, 17.82°±0.2°, 18.20°±0.2°, 18.46°±0.2°, 18.69°±0.2°, 19.21°±0.2°, 19.47°±0.2°, 19.72°±0.2°, 20.14°±0.2°, 20.49°±0.2°, 20.98°±0.2°, 21.56°±0.2°, 21.91°±0.2°, 23.23°±0.2°, 23.89°±0.2°, 24.45°±0.2°, 24.60°±0.2°, 25.46°±0.2°, 26.28°±0.2°, 26.53°±0.2°, 26.98°±0.2°, 27.30°±0.2°, 27.71°±0.2°, 28.38°±0.2°, 29.09°±0.2°, 29.47°±0.2°, 30.11°±0.2°, 30.74°±0.2°, 31.28°±0.2°, 31.54°±0.2°, 33.26°±0.2°, 33.85°±0.2°, 34.60°±0.2°, 35.36°±0.2°, 35.74°±0.2°, and 36.69°±0.2°.

4. The acid addition salt of claim 1, wherein the salt is the benzene sulfonate crystalline I, and the benzene sulfonate crystalline I has a differential scanning calorimetry thermogram comprising an endothermic peak at 189.55° C.±3° C.

5. The acid addition salt of claim 1, wherein the salt is the benzene sulfonate crystalline I, and the benzene sulfonate crystalline I has an X-ray powder diffraction pattern that is substantially the same as shown in FIG. 3.

6. The acid addition salt of claim 1, wherein the salt is the benzene sulfonate crystalline I, and the benzene sulfonate crystalline I has a differential scanning calorimetry thermogram that is substantially the same as shown in FIG. 10.

7. The acid addition salt of claim 1, wherein the salt is the benzene sulfonate crystalline II and has at least one of the following characteristics:
  (a) the X-ray powder diffraction pattern further comprises one or more peaks expressed as 2θ at 9.22°±0.2°, 17.49°±0.2°, 19.57°±0.2°, 20.18°±0.2°, and 21.23°±0.2°;
  (b) the X-ray powder diffraction pattern further comprises one or more peaks expressed as 6.66°±0.2°, 9.22°±0.2°, 12.31°±0.2°, 12.97°±0.2°, 15.33°±0.2°, 16.17°±0.2°, 16.48°±0.2°, 17.49°±0.2°, 18.53°±0.2°, 19.57°±0.2°, 20.18°±0.2°, 21.23°±0.2°, 23.69°±0.2°, 24.18°±0.2°, 24.66°±0.2°, 25.52°±0.2°, 26.46°±0.2°, 27.78°±0.2°, 28.34°±0.2°, 29.15°±0.2°, 30.64°±0.2°, 30.99°±0.2°, 32.45°±0.2°, 33.93°±0.2°, 34.70°±0.2°, 35.48°±0.2°, and 38.57°±0.2°;
  (c) a differential scanning calorimetry thermogram comprising endothermic peaks at 167.42° C.±3° C. and 173.39° C.±3° C.;
  (d) the X-ray powder diffraction pattern is substantially the same as shown in FIG. 4; and
  (e) a differential scanning calorimetry thermogram that is substantially the same as shown in FIG. 11.

8. The acid addition salt of claim 1, wherein the salt is the benzene sulfonate crystalline III and has at least one of the following characteristics:
  (a) the X-ray powder diffraction pattern further comprises one or more peaks expressed as 2θ at 15.33°±0.2°, 18.21°±0.2°, 18.46°±0.2°, 20.29°±0.2°, 21.38°±0.2°, and 22.99°±0.2°;
  (b) the X-ray powder diffraction pattern further comprises one or more peaks expressed as 2θ at 6.61°±0.2°, 11.36°±0.2°, 11.89°±0.2°, 12.31°±0.2°, 12.72°±0.2°, 12.95°±0.2°, 13.17°±0.2°, 13.71°±0.2°, 14.64°±0.2°, 15.33°±0.2°, 16.49°±0.2°, 17.11°±0.2°, 18.21°±0.2°, 18.46°±0.2°, 19.49°±0.2°, 20.29°±0.2°, 21.38°±0.2°, 22.99°±0.2°, 24.10°±0.2°, 24.37°±0.2°, 24.89°±0.2°, 25.61°±0.2°, 26.52°±0.2°, 27.63°±0.2°, 28.03°±0.2°, 29.07°±0.2°, 29.49°±0.2°, 30.22°±0.2°, 30.92°±0.2°, 31.16°±0.2°, 32.55°±0.2°, 33.53°±0.2°, 34.96°±0.2°, 37.51°±0.2°, and 38.94°±0.2°;
  (c) a differential scanning calorimetry thermogram comprising an endothermic peak at 139.64° C.±3° C.;
  (d) the X-ray powder diffraction pattern is substantially the same as shown in FIG. 5; and
  (e) a differential scanning calorimetry thermogram that is substantially the same as shown in FIG. 12.

9. The acid addition salt of claim 1, wherein the salt is the benzene sulfonate crystalline IV or the benzene sulfonate crystalline V;
  when the salt is the benzene sulfonate crystalline IV, the salt has at least one of the following characteristics:
    (a) the X-ray powder diffraction pattern further comprises one or more peaks expressed as 2θ at 16.42°±0.2°, 18.31°±0.2°, 19.34°±0.2°, 20.05°±0.2°, and 27.75°±0.2°;
    (b) the X-ray powder diffraction pattern further comprises one or more peaks expressed as 2θ at 6.07°±0.2°, 9.15°±0.2°, 11.28°±0.2°, 12.22°±0.2°, 12.47°±0.2°, 12.85°±0.2°, 13.71°±0.2°, 14.36°±0.2°, 15.21°±0.2°, 15.67°±0.2°, 16.11°±0.2°, 16.42°±0.2°, 17.38°±0.2°, 17.84°±0.2°, 18.31°±0.2°, 19.34°±0.2°, 19.47°±0.2°, 19.69°±0.2°, 20.05°±0.2°, 21.56°±0.2°, 21.80°±0.2°, 23.14°±0.2°, 23.68°±0.2°, 24.01°±0.2°, 24.29°±0.2°, 24.62°±0.2°, 25.34°±0.2°, 26.01°±0.2°, 26.36°±0.2°, 26.96°±0.2°, 27.48°±0.2°, 27.75°±0.2°, 28.23°±0.2°, 28.45°±0.2°, 29.06°±0.2°, 29.18°±0.2°, 29.40°±0.2°, 29.74°±0.2°, 30.48°±0.2°, 30.64°±0.2°, 31.07°±0.2°, 31.61°±0.2°, 32.56°±0.2°, 33.16°±0.2°, and 33.44°±0.2°;
    (c) a differential scanning calorimetry thermogram comprising endothermic peaks at 160.59° C.±3° C. and 203.47° C.±3° C.;
    (d) the X-ray powder diffraction pattern is substantially the same as shown in FIG. 6; and
    (e) a differential scanning calorimetry thermogram that is substantially the same as shown in FIG. 13; or
  when the salt is the benzene sulfonate crystalline V, the salt has at least one of the following characteristics:
    (1) the X-ray powder diffraction pattern further comprises one or more peaks expressed as 2θ at 20.16°±0.2°, 21.66°±0.2°, 22.24°±0.2°, 22.60°±0.2°, and 23.13°±0.2°;
    (2) the X-ray powder diffraction pattern further comprises one or more peaks expressed as 2θ at 9.62°±0.2°, 12.08°±0.2°, 13.04°±0.2°, 14.22°±0.2°, 14.60°±0.2°, 14.87°±0.2°, 15.90°±0.2°, 16.33°±0.2°, 16.66°±0.2°, 18.18°±0.2°, 20.16°±0.2°, 20.89°±0.2°, 21.66°±0.2°, 22.24°±0.2°, 22.60°±0.2°, 23.13°±0.2°, 23.60°±0.2°, 24.09°±0.2°, 24.33°±0.2°, 24.55°±0.2°, 25.17°±0.2°, 26.17°±0.2°, 27.08°±0.2°, 27.50°±0.2°, 28.73°±0.2°, 29.09°±0.2°, 29.62°±0.2°, 30.50°±0.2°, 31.62°±0.2°, 32.71°±0.2°, 33.87°±0.2°, 34.62°±0.2°, 36.64°±0.2°, 37.46°±0.2°, 38.22°±0.2°, and 39.94°±0.2°;
    (3) a differential scanning calorimetry thermogram comprising an endothermic peak at 202.15° C.±3° C.;
    (4) the X-ray powder diffraction pattern is substantially the same as shown in FIG. 7; and
    (5) a differential scanning calorimetry thermogram that is substantially the same as shown in FIG. 14.

10. A pharmaceutical composition comprising the acid addition salt of claim 1, and a pharmaceutically acceptable carrier, excipient, diluent, adjuvant or a combination thereof.

11. The pharmaceutical composition of claim 10 further comprising at least one other active agent used for treating proliferative diseases, autoimmune diseases or inflammatory diseases, wherein the at least one other active agent is selected from the group consisting of chemotherapeutic drug, antiproliferative agent, immunosuppressor, immunologic stimulant, anti-inflammatory reagent, agent for treating atherosclerosis, agent for treating pulmonary fibrosis, CDK4/6 kinase inhibitor, ABL inhibitor, ABL/Scr inhibitor, aurora kinase inhibitor, non-ATP competitive inhibitor of BCR-ABL, c-KIT mutation inhibitor, RET inhibitor, PDGFR inhibitor, VEGFR inhibitor, FLT3 inhibitor, and FLT3-ITD inhibitor.

12. The pharmaceutical composition of claim 10 further comprising at least one other active agent used for treating proliferative diseases, autoimmune diseases or inflammatory diseases, wherein the at least one other active agent is selected from the group consisting of chlorambucil, melphalan, cyclophosphamide, ifosfamide, busulfan, carmustine, lomustine, streptozotocin, cis-platinum, carboplatin, oxaliplatin, dacarbazine, temozolomide, procarbozine, methotrexate, fluorouracil, cytosine arabinoside, gemcitabine, purinethol, fludarabine, vinblastine, vincristine, vinorelbine, paclitaxel, docetaxel, topotecan, irinotecan, etoposide, trabectedin, dactinomycin, doxorubicin, pharmorubicin, daunomycin, mitoxantrone, bleomycin, mitomycin C, ixabepilone, tamoxifen, flutamide, gonadorelin analogue, megestrol acetate, prednisone, dexamethasone, methylprednisolone, thalidomide, interferon α, calcium folinate, sirolimus, temsirolimus, everolimus, afatinib, alisertib, amuvatinib, apatinib, axitinib, bortezomib, bosutinib, brivanib, cabozantinib, cediranib, crenolanib, crizotinib, dabrafenib, dacomitinib, danusertib, dasatinib, dovitinib, erlotinib, foretinib, ganetespib, gefitinib, ibrutinib, icotinib, imatinib, iniparib, lapatinib, lenvatinib, linifanib, linsitinib, masitinib, momelotinib, motesanib, neratinib, nilotinib, niraparib, oprozomib, olaparib, pazopanib, pictilisib, ponatinib, quizartinib, regorafenib, rigosertib, rucaparib, ruxolitinib, saracatinib, saridegib, sorafenib, sunitinib, tasocitinib, telatinib, tivantinib, tivozanib, tofacitinib, trametinib, vandetanib, veliparib, zelboraf, vismodegib, volasertib, alemtuzumab, bevacizumab, brentuximab vedotin, catumaxomab, cetuximab, denosumab, gemtuzumab, ipilimumab, nimotuzumab, ofatumumab, panitumumab, rituximab, tositumomab, trastuzumab, cabozantinib, ponatinib, midostaurin, pacritinib, gilteritinib, AKN-028, AT-9283, crenolanib, ENMD-2076, famitinib, dovitinib, PLX-3397, palbociclib, abemaciclib, ribociclib, rigosertib sodium, selinexor, roniciclib, AT-7519, seliciclib, and alvocidib.

13. A method of managing, treating, remitting or lessening proliferative diseases, autoimmune diseases or inflammatory diseases in a patient comprising administering the acid addition salt of claim 1 to the patient.

14. A method of managing, treating, remitting or lessening proliferative diseases, autoimmune diseases or inflammatory diseases in a patient comprising administering the pharmaceutical composition of claim 10 to the patient.

15. The method of claim 13, wherein the proliferative disease is gastrointestinal stromal tumor, acute myelocytic leukemia, mutated chronic myeloid leukemia, acute lymphoblastic leukemia, leukaemia, chronic lymphocytic leukemia, primary macroglobulinemia, monocytic leukemia, leukemoid reaction, aplastic anemia, hemacelinosis, secondary or benign monoclonal gammopathy, colorectal cancer, gastric cancer, mammary cancer, lung cancer, liver cancer, prostatic cancer, pancreatic cancer, cancerous goiter, renal carcinoma, cerebroma, neck cancer, central nervous system cancer, malignant glioma, myeloproliferative disease, malignant histiocytosis, lymphoma, non lymphoreticular system tumor, multiple myeloma, granulocytic sarcoma, solitary plasmacytoma, malignant lymphoma, osteolytic lesion, lymphoblastoma, non-Hodgkin lymphoma, acute histiocytosis, Hodgkin's lymphoma, colon cancer, rectal cancer, small cell lung cancer, neuroblastoma, neuroendocrine cell tumor, islet cell tumor, medullary thyroid carcinoma, melanoma, retinoblastoma, uterine cancer, ovarian cancer, head and neck squamous cell carcinoma, alimentary canal malignancy, non-small cell lung cancer, cervical cancer, testiculoma, bladder cancer, myeloma or complications related to acute myelocytic leukemia;

the autoimmune disease is rheumatic arthritis, osteoarthralgia, lupus, multiple sclerosis, thyroiditis, type I diabetes, sarcoidosis, inflammatory bowel disease, Crohn's disease or systemic lupus;

the inflammatory disease is diverticulitis, colitis, pancreatitis, hepatitis, chronic hepatitis, cirrhosis, cholecystitis or chronic inflammation.

16. A drug combination comprising the acid addition salt of claim 1 and at least one other active agent used for treating proliferative diseases, autoimmune diseases or inflammatory diseases; wherein the at least one other active agent is selected from the group consisting of chemotherapeutic drug, antiproliferative agent, immunosuppressor, immunologic stimulant, anti-inflammatory reagent, CDK4/6 kinase inhibitor, ABL inhibitor, ABL/Scr inhibitor, aurora kinase inhibitor, non-ATP competitive inhibitor of BCR-ABL, c-KIT mutation inhibitor, RET inhibitor, PDGFR inhibitor, VEGFR inhibitor, FLT3 inhibitor, and FLT3-ITD inhibitor.

17. A drug combination comprising the pharmaceutical composition of claim 10 and at least one other active agent used for treating proliferative diseases, autoimmune diseases or inflammatory diseases; wherein the at least one other active agent is selected from the group consisting of chemotherapeutic drug, antiproliferative agent, immunosuppressor, immunologic stimulant, anti-inflammatory reagent, CDK4/6 kinase inhibitor, ABL inhibitor, ABL/Scr inhibitor, aurora kinase inhibitor, non-ATP competitive inhibitor of BCR-ABL, c-KIT mutation inhibitor, RET inhibitor, PDGFR inhibitor, VEGFR inhibitor, FLT3 inhibitor, and FLT3-ITD inhibitor.

18. A method of managing, treating, remitting or lessening a disease caused by mutation of c-KIT or mediation of RET, PDGFR, VEGFR, Bcr-ABL, FLT3 or FLT3-ITD in a patient, the method comprising administering the acid addition salt of claim 1 to the patient.

* * * * *